US011414683B2

United States Patent
De Bruijn

(10) Patent No.: US 11,414,683 B2
(45) Date of Patent: Aug. 16, 2022

(54) ACETIC ACID CONSUMING STRAIN

(71) Applicant: DSM IP ASSETS B.V., Heerlen (NL)

(72) Inventor: Hans Marinus Charles Johannes De Bruijn, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/650,330

(22) PCT Filed: Sep. 25, 2018

(86) PCT No.: PCT/EP2018/075962
§ 371 (c)(1),
(2) Date: Mar. 24, 2020

(87) PCT Pub. No.: WO2019/063544
PCT Pub. Date: Apr. 4, 2019

(65) Prior Publication Data
US 2020/0270645 A1 Aug. 27, 2020

(30) Foreign Application Priority Data

Sep. 26, 2017 (EP) ...................... 17193046

(51) Int. Cl.
| | |
|---|---|
| *C12P 7/10* | (2006.01) |
| *C12N 1/18* | (2006.01) |
| *C12R 1/865* | (2006.01) |
| *C07K 14/245* | (2006.01) |
| *C12N 9/12* | (2006.01) |
| *C12N 9/00* | (2006.01) |
| *C12N 9/10* | (2006.01) |
| *C12N 9/04* | (2006.01) |
| *C12N 9/88* | (2006.01) |
| *C12N 9/02* | (2006.01) |
| *C12N 9/16* | (2006.01) |
| *C12N 1/19* | (2006.01) |

(52) U.S. Cl.
CPC .............. *C12P 7/10* (2013.01); *C07K 14/245* (2013.01); *C12N 9/0006* (2013.01); *C12N 9/0008* (2013.01); *C12N 9/1025* (2013.01); *C12N 9/1217* (2013.01); *C12N 9/16* (2013.01); *C12N 9/88* (2013.01); *C12N 9/93* (2013.01); *C12N 1/185* (2021.05); *C12R 2001/865* (2021.05); *C12Y 101/01001* (2013.01); *C12Y 101/01002* (2013.01); *C12Y 101/01006* (2013.01); *C12Y 101/01008* (2013.01); *C12Y 102/0101* (2013.01); *C12Y 102/01003* (2013.01); *C12Y 203/01008* (2013.01); *C12Y 207/01029* (2013.01); *C12Y 207/02012* (2013.01); *C12Y 401/02009* (2013.01); *C12Y 401/02022* (2013.01); *C12Y 602/01001* (2013.01)

(58) Field of Classification Search
None
See application file for complete search history.

(56) References Cited

U.S. PATENT DOCUMENTS

| | | | | |
|---|---|---|---|---|
| 10,280,437 | B2 * | 5/2019 | Ikeo .......................... | C12P 7/10 |
| 2015/0176032 | A1 * | 6/2015 | De Bont ........ | C12Y 101/01006 |
| | | | | 435/161 |
| 2016/0177342 | A1 * | 6/2016 | Chao ....................... | C12N 1/16 |
| | | | | 435/255.7 |
| 2020/0024619 | A1 * | 1/2020 | De Waal ........ | C12Y 401/02009 |

FOREIGN PATENT DOCUMENTS

| | | | |
|---|---|---|---|
| WO | 2011149353 A1 | 12/2011 | |
| WO | WO-2013081456 A2 * | 6/2013 | ............... C12P 7/10 |
| WO | 2015075316 A1 | 5/2015 | |

OTHER PUBLICATIONS

Taherzadeh et al., Acetic acid friend or foe in anaerobic batch conversion of glucose to ethanol by *Saccharomyces cerevisiae*, Chem. Eng. Sci. 52, 1997, 2653-59. (Year: 1997).*
Namazian et al., Calculations of pKa values of carboxylic acids in aqueous solution using density functional theory, J. Chem. Thermodynamics 38, 2006, 1495-502. (Year: 2006).*
Acetic Acid, Material Safety Data Sheet (MSDS), Pioneer Forensics, 2012. (Year: 2012).*
Zhao et al., Bioconversion of corn stover hydrolysate to ethanol by a recombinant yeast strain, Fuel Process. Technol. 91, 2010, 1807-11. (Year: 2010).*
Pena et al., Effects of high medium pH on growth, metabolism and transport in *Saccharomyces cerevisiae*, FEMS Yeast Res. 15, 2015, fou005. (Year: 2015).*
PCT International Search Report for PCT/EP2018/075962, dated Jul. 12, 2018.
Bellissimi, Eleonora, et al. "Effects of acetic acid on the kinetics of xylose fermentation by an engineered, xylose-somerase-based *Saccharomyces cerevisiae* strain." FEMS yeast research, (2009), vol. 9, No. 3: 358-364.
Casey, Elizabeth, et al. "Effect of acetic acid and pH on the cofermentation of glucose and xylose to ethanol by a genetically engineered strain of *Saccharomyces cerevisiae*." FEMS yeast research, (2010), vol. 10, No. 4: 385-393.

(Continued)

*Primary Examiner* — Robert B Mondesi
*Assistant Examiner* — Todd M Epstein
(74) *Attorney, Agent, or Firm* — McBee Moore & Vanik IP, LLC; Susan McBee; Chester Moore

(57) ABSTRACT

The invention describes a process for the production of ethanol from a composition comprising glucose and between 50 µM and 100 mM acetic acid, said process comprising fermenting said composition in the presence of a recombinant yeast which is capable to convert acetic acid anaerobically; maintaining the amount of undissociated acetic acid at a value of at least 50 µM; and recovering the ethanol. Said process is useful for both starch and cellulosic based, acetic acid containing hydrolysates and advantageously results in a greater consumption of acetic acid and thus higher ethanol yields.

12 Claims, No Drawings

Specification includes a Sequence Listing.

(56) References Cited

OTHER PUBLICATIONS

Greetham, D., et al. "Development of a phenotypic assay for characterisation of ethanologenic yeast strain sensitivity to inhibitors released from lignocellulosic feedstocks." Journal of industrial microbiology & biotechnology, (2014), vol. 41, No. 6: 931-945.

Helle, Steve, et al. "Effect of inhibitory compounds found in biomass hydrolysates on growth and xylose fermentation by a genetically engineered strain of S. cerevisiae." Enzyme and Microbial Technology, (2003), vol. 33, No. 6: 786-792.

Henningsen, Brooks M., et al. "Increasing anaerobic acetate consumption and ethanol yields in Saccharomyces cerevisiae with NADPH-specific alcohol dehydrogenase." Appl. Environ. Microbiol., (2015), vol. 81, No. 23: 8108-8117.

Nygard, Yvonne, et al. "The diverse role of Pdr12 in resistance to weak organic acids." Yeast, (2014), vol. 31, No. 6: 219-232.

Zhang, Jun-Guo, et al. "Improvement of acetic acid tolerance and fermentation performance of Saccharomyces cerevisiae by disruption of the FPS1 aquaglyceroporin gene." Biotechnology letters, (2011), vol. 33, No. 2: 277-284.

\* cited by examiner

SEQUENCE LISTING

<160> NUMBER OF SEQ ID NOS: 30

<210> SEQ ID NO 1
<211> LENGTH: 891
<212> TYPE: PRT
<213> ORGANISM: Escherichia coli
<220> FEATURE:
<221> NAME/KEY: MISC_FEATURE
<222> LOCATION: (1)..(891)
<223> OTHER INFORMATION: E. coli bifunctional NAD+ dependent acetylating
      acetaldehyd/alcohol dehydrogenase (E. coli adhE) amino acid
      sequence

<400> SEQUENCE: 1

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Leu Ala Ala Asp Ala Arg Ile Pro
        35                  40                  45

Leu Ala Lys Met Ala Val Ala Glu Ser Gly Met Gly Ile Val Glu Asp
50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
            85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
        130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

```
Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750
```

Ala Asn Asp Asn Pro Thr Lys Gln Thr Ala Phe Ser Gln Tyr Asp Arg
        755                 760                 765

Pro Gln Ala Arg Arg Tyr Ala Glu Ile Ala Asp His Leu Gly Leu
770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
        850                 855                 860

Arg Asp Tyr Val Glu Gly Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 2
<211> LENGTH: 467
<212> TYPE: PRT
<213> ORGANISM: Escherichia coli
<220> FEATURE:
<221> NAME/KEY: MISC_FEATURE
<222> LOCATION: (1)..(467)
<223> OTHER INFORMATION: E. coli ethanolamine utilizing protein
      (Ec_eutE) amino acid sequence

<400> SEQUENCE: 2

Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
                20                  25                  30

Phe Ala Ser Leu Asp Asp Ala Val Ala Ala Lys Val Ala Gln Gln
            35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
                260                 265                 270

Lys Val Leu Ile Val Val Asp Ser Val Ala Asp Glu Leu Met Arg Leu
            275                 280                 285

Met Glu Gly Gln His Ala Val Lys Leu Thr Ala Glu Gln Ala Gln Gln
            290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
            355                 360                 365

Pro Val Val Arg Val Ala Asn Val Ala Asp Ala Ile Ala Leu Ala Val
370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
            435                 440                 445

Ala Arg Thr Phe Val Arg Leu Arg Arg Cys Val Leu Val Asp Ala Phe
450                 455                 460

Arg Ile Val
465

<210> SEQ ID NO 3
<211> LENGTH: 455
<212> TYPE: PRT
<213> ORGANISM: Lactobacillus plantarum
<220> FEATURE:
<221> NAME/KEY: MISC_FEATURE
<222> LOCATION: (1)..(455)
<223> OTHER INFORMATION: L. plantarum acetaldehyde dehydrogenase
      (Lpla_acdH) amino acid sequence

<400> SEQUENCE: 3

Met Leu Lys Glu Met Glu Glu Thr Thr Val Ser Arg Ser Ile Asp Arg
1               5                   10                  15

Leu Val Leu Asn Ala Ser Leu Ala Ala Asn Arg Leu Glu Val Met Asp
                20                  25                  30

Gln Ser Gln Val Asp Gln Ala Val Ala Met Ala Arg Ala Ala His
            35                  40                  45

Ala Ala Arg Gly Met Leu Ala Ala Met Ala Val Glu Glu Thr Gly Arg
        50                  55                  60

Gly Asn Tyr Arg Asp Lys Val Ala Lys Asn Asp Phe Ala Ala Lys Asn
65                  70                  75                  80

Val Tyr Asn Tyr Ile Lys Asp Asp Lys Thr Val Gly Ile Ile Asn Asp
            85                  90                  95

Asp Pro Val Ser Gly Val Met Lys Val Ala Glu Pro Val Gly Ile Ile
            100                 105                 110

Ala Gly Val Thr Pro Val Thr Asn Pro Thr Ser Thr Val Ile Phe Asn
            115                 120                 125

Ala Met Leu Ala Leu Lys Thr Arg Asn Pro Ile Ile Phe Gly Phe His
        130                 135                 140

Pro Phe Ala Gln Lys Ser Cys Val Glu Thr Gly Arg Ile Ile Arg Asp
145                 150                 155                 160

Ala Ala Ile Ala Ser Gly Ala Pro Lys Asp Trp Ile Gln Trp Ile Lys
                165                 170                 175

Thr Pro Ser Leu Glu Ala Thr Asn Thr Leu Met Asn His Pro Gly Val
            180                 185                 190

Ala Thr Ile Ile Ala Thr Gly Gly Ala Gly Met Val Lys Thr Ala Tyr
        195                 200                 205

Ser Thr Gly Lys Pro Ala Leu Gly Val Gly Pro Gly Asn Val Pro Cys
    210                 215                 220

Phe Ile Glu Gln Thr Ala Asp Ile Gln Gln Ala Val Ser Asp Val Val
225                 230                 235                 240

Thr Ser Lys Ser Phe Asp Asn Gly Met Ile Cys Ala Ser Glu Ser Asn
                245                 250                 255

Leu Ile Val Ala Asp Gln Ile Tyr Asp Gln Val Lys Arg Glu Leu Ser
            260                 265                 270

His Asn Gly Val Tyr Phe Val Gly Thr Glu Asn Phe Lys Ala Leu Glu
        275                 280                 285

Ala Thr Val Met Asn Leu Asp Lys Gln Ala Val Asp Pro Lys Val Ala
    290                 295                 300

Gly Gln Thr Pro Trp Gln Ile Ala Gln Trp Ala Gly Phe Asp Val Pro
305                 310                 315                 320

Ser Asp Thr Lys Val Leu Ala Val Glu Leu Pro Ser Ile Gly Gly Asp
                325                 330                 335

Gln Val Leu Ser Arg Glu Lys Leu Ser Pro Val Leu Ala Val Val His
            340                 345                 350

Ala Lys Asp Thr Glu Ala Gly Phe Asn Leu Met Lys Arg Ser Leu Ala
        355                 360                 365

Leu Gly Gly Leu Gly His Thr Ala Ala Leu His Thr Asp Glu Ala
    370                 375                 380

Val Met Asn Lys Phe Ala Leu Glu Met Thr Ala Cys Arg Ala Leu Ile
385                 390                 395                 400

Asn Val Pro Ser Ser Gln Gly Ala Ile Gly Tyr Lys Tyr Asp Asn Val
                405                 410                 415

Ala Pro Ser Leu Thr Leu Gly Cys Gly Thr Trp Gly His Asn Ser Ile
            420                 425                 430

Ser His Asn Leu Glu Asp Trp Asp Leu Leu Asn Ile Lys Thr Val Ala
        435                 440                 445

Lys Arg Leu Thr Lys Ile Arg
    450                 455

<210> SEQ ID NO 4
<211> LENGTH: 469
<212> TYPE: PRT
<213> ORGANISM: Listeria innocua
<220> FEATURE:

<210> NAME/KEY: MISC_FEATURE
<222> LOCATION: (1)..(469)
<223> OTHER INFORMATION: L. innocua acetaldehyde dehydrogenase
      (Linn_acdH) amino acid sequence

<400> SEQUENCE: 4

```
Met Glu Ser Leu Glu Leu Glu Gln Leu Val Lys Lys Val Leu Glu
1               5                   10                  15

Lys Leu Ala Glu Gln Lys Glu Val Pro Thr Lys Thr Thr Gln Gly
            20                  25                  30

Ala Lys Ser Gly Val Phe Asp Thr Val Asp Glu Ala Val Gln Ala Ala
            35                  40                  45

Val Ile Ala Gln Asn Cys Tyr Lys Glu Lys Ser Leu Glu Glu Arg Arg
50                  55                  60

Asn Val Val Lys Ala Ile Arg Glu Ala Leu Tyr Pro Glu Ile Glu Thr
65                  70                  75                  80

Ile Ala Thr Arg Ala Val Ala Glu Thr Gly Met Gly Asn Val Thr Asp
                85                  90                  95

Lys Ile Leu Lys Asn Thr Leu Ala Ile Glu Lys Thr Pro Gly Val Glu
            100                 105                 110

Asp Leu Tyr Thr Glu Val Ala Thr Gly Asp Asn Gly Met Thr Leu Tyr
            115                 120                 125

Glu Leu Ser Pro Tyr Gly Val Ile Gly Ala Val Ala Pro Ser Thr Asn
130                 135                 140

Pro Thr Glu Thr Leu Ile Cys Asn Ser Ile Gly Met Leu Ala Ala Gly
145                 150                 155                 160

Asn Ala Val Phe Tyr Ser Pro His Pro Gly Ala Lys Asn Ile Ser Leu
                165                 170                 175

Trp Leu Ile Glu Lys Leu Asn Thr Ile Val Arg Asp Ser Cys Gly Ile
            180                 185                 190

Asp Asn Leu Ile Val Thr Val Ala Lys Pro Ser Ile Gln Ala Ala Gln
            195                 200                 205

Glu Met Met Asn His Pro Lys Val Pro Leu Leu Val Ile Thr Gly Gly
210                 215                 220

Pro Gly Val Val Leu Gln Ala Met Gln Ser Gly Lys Lys Val Ile Gly
225                 230                 235                 240

Ala Gly Ala Gly Asn Pro Pro Ser Ile Val Asp Glu Thr Ala Asn Ile
                245                 250                 255

Glu Lys Ala Ala Ala Asp Ile Val Asp Gly Ala Ser Phe Asp His Asn
            260                 265                 270

Ile Leu Cys Ile Ala Glu Lys Ser Val Val Ala Val Asp Ser Ile Ala
            275                 280                 285

Asp Phe Leu Leu Phe Gln Met Glu Lys Asn Gly Ala Leu His Val Thr
290                 295                 300

Asn Pro Ser Asp Ile Gln Lys Leu Glu Lys Val Ala Val Thr Asp Lys
305                 310                 315                 320

Gly Val Thr Asn Lys Lys Leu Val Gly Lys Ser Ala Thr Glu Ile Leu
                325                 330                 335

Lys Glu Ala Gly Ile Ala Cys Asp Phe Thr Pro Arg Leu Ile Ile Val
            340                 345                 350

Glu Thr Glu Lys Ser His Pro Phe Ala Thr Val Glu Leu Leu Met Pro
            355                 360                 365

Ile Val Pro Val Val Arg Val Pro Asp Phe Asp Glu Ala Leu Glu Val
370                 375                 380
```

```
Ala Ile Glu Leu Glu Gln Gly Leu His His Thr Ala Thr Met His Ser
385                 390                 395                 400

Gln Asn Ile Ser Arg Leu Asn Lys Ala Ala Arg Asp Met Gln Thr Ser
        405                 410                 415

Ile Phe Val Lys Asn Gly Pro Ser Phe Ala Gly Leu Gly Phe Arg Gly
            420                 425                 430

Glu Gly Ser Thr Thr Phe Thr Ile Ala Thr Pro Thr Gly Glu Gly Thr
                435                 440                 445

Thr Thr Ala Arg His Phe Ala Arg Arg Arg Cys Val Leu Thr Asp
        450                 455                 460

Gly Phe Ser Ile Arg
465
```

<210> SEQ ID NO 5
<211> LENGTH: 869
<212> TYPE: PRT
<213> ORGANISM: Staphylococcus aureus
<220> FEATURE:
<221> NAME/KEY: MISC_FEATURE
<222> LOCATION: (1)..(869)
<223> OTHER INFORMATION: S. aureus acetaldehyde/alcohol dehydrogenase
      (Saur_adhE) amino acid sequence

<400> SEQUENCE: 5

```
Met Leu Thr Ile Pro Glu Lys Glu Asn Arg Gly Ser Lys Glu Gln Glu
1               5                   10                  15

Val Ala Ile Met Ile Asp Ala Leu Ala Asp Lys Gly Lys Lys Ala Leu
            20                  25                  30

Glu Ala Leu Ser Lys Lys Ser Gln Glu Glu Ile Asp His Ile Val His
        35                  40                  45

Gln Met Ser Leu Ala Ala Val Asp Gln His Met Val Leu Ala Lys Leu
50                  55                  60

Ala His Glu Glu Thr Gly Arg Gly Ile Tyr Glu Asp Lys Ala Ile Lys
65                  70                  75                  80

Asn Leu Tyr Ala Ser Glu Tyr Ile Trp Asn Ser Ile Lys Asp Asn Lys
                85                  90                  95

Thr Val Gly Ile Ile Gly Glu Asp Lys Glu Lys Gly Leu Thr Tyr Val
            100                 105                 110

Ala Glu Pro Ile Gly Val Ile Cys Gly Val Thr Pro Thr Thr Asn Pro
        115                 120                 125

Thr Ser Thr Thr Ile Phe Lys Ala Met Ile Ala Ile Lys Thr Gly Asn
    130                 135                 140

Pro Ile Ile Phe Ala Phe His Pro Ser Ala Gln Glu Ser Ser Lys Arg
145                 150                 155                 160

Ala Ala Glu Val Val Leu Glu Ala Ala Met Lys Ala Gly Ala Pro Lys
                165                 170                 175

Asp Ile Ile Gln Trp Ile Glu Val Pro Ser Ile Glu Ala Thr Lys Gln
            180                 185                 190

Leu Met Asn His Lys Gly Ile Ala Leu Val Leu Ala Thr Gly Gly Ser
        195                 200                 205

Gly Met Val Lys Ser Ala Tyr Ser Thr Gly Lys Pro Ala Leu Gly Val
    210                 215                 220

Gly Pro Gly Asn Val Pro Ser Tyr Ile Glu Lys Thr Ala His Ile Lys
225                 230                 235                 240

Arg Ala Val Asn Asp Ile Ile Gly Ser Lys Thr Phe Asp Asn Gly Met
                245                 250                 255
```

```
Ile Cys Ala Ser Glu Gln Val Val Ile Asp Lys Glu Ile Tyr Lys
            260                 265                 270

Asp Val Thr Asn Glu Phe Lys Ala His Gln Ala Tyr Phe Val Lys Lys
        275                 280                 285

Asp Glu Leu Gln Arg Leu Glu Asn Ala Ile Met Asn Glu Gln Lys Thr
    290                 295                 300

Gly Ile Lys Pro Asp Ile Val Gly Lys Ser Ala Val Glu Ile Ala Glu
305                 310                 315                 320

Leu Ala Gly Ile Pro Val Pro Glu Asn Thr Lys Leu Ile Ile Ala Glu
                325                 330                 335

Ile Ser Gly Val Gly Ser Asp Tyr Pro Leu Ser Arg Glu Lys Leu Ser
        340                 345                 350

Pro Val Leu Ala Leu Val Lys Ala Gln Ser Thr Lys Gln Ala Phe Gln
    355                 360                 365

Ile Cys Glu Asp Thr Leu His Phe Gly Gly Leu Gly His Thr Ala Val
370                 375                 380

Ile His Thr Glu Asp Glu Thr Leu Gln Lys Asp Phe Gly Leu Arg Met
385                 390                 395                 400

Lys Ala Cys Arg Val Leu Val Asn Thr Pro Ser Ala Val Gly Gly Ile
                405                 410                 415

Gly Asp Met Tyr Asn Glu Leu Ile Pro Ser Leu Thr Leu Gly Cys Gly
        420                 425                 430

Ser Tyr Gly Arg Asn Ser Ile Ser His Asn Val Ser Ala Thr Asp Leu
    435                 440                 445

Leu Asn Ile Lys Thr Ile Ala Lys Arg Arg Asn Asn Thr Gln Ile Phe
450                 455                 460

Lys Val Pro Ala Gln Ile Tyr Phe Glu Glu Asn Ala Ile Met Ser Leu
465                 470                 475                 480

Thr Thr Met Asp Lys Ile Glu Lys Val Met Ile Val Cys Asp Pro Gly
                485                 490                 495

Met Val Glu Phe Gly Tyr Thr Lys Thr Val Glu Asn Val Leu Arg Gln
        500                 505                 510

Arg Thr Glu Gln Pro Gln Ile Lys Ile Phe Ser Glu Val Glu Pro Asn
    515                 520                 525

Pro Ser Thr Asn Thr Val Tyr Lys Gly Leu Glu Met Met Val Asp Phe
530                 535                 540

Gln Pro Asp Thr Ile Ile Ala Leu Gly Gly Gly Ser Ala Met Asp Ala
545                 550                 555                 560

Ala Lys Ala Met Trp Met Phe Phe Glu His Pro Glu Thr Ser Phe Phe
                565                 570                 575

Gly Ala Lys Gln Lys Phe Leu Asp Ile Gly Lys Arg Thr Tyr Lys Ile
        580                 585                 590

Gly Met Pro Glu Asn Ala Thr Phe Ile Cys Ile Pro Thr Thr Ser Gly
    595                 600                 605

Thr Gly Ser Glu Val Thr Pro Phe Ala Val Ile Thr Asp Ser Glu Thr
610                 615                 620

Asn Val Lys Tyr Pro Leu Ala Asp Phe Ala Leu Thr Pro Asp Val Ala
625                 630                 635                 640

Ile Ile Asp Pro Gln Phe Val Met Ser Val Pro Lys Ser Val Thr Ala
                645                 650                 655

Asp Thr Gly Met Asp Val Leu Thr His Ala Met Glu Ser Tyr Val Ser
        660                 665                 670
```

Val Met Ala Ser Asp Tyr Thr Arg Gly Leu Ser Leu Gln Ala Ile Lys
        675                 680                 685

Leu Thr Phe Glu Tyr Leu Lys Ser Ser Val Glu Lys Gly Asp Lys Val
        690                 695                 700

Ser Arg Glu Lys Met His Asn Ala Ser Thr Leu Ala Gly Met Ala Phe
705                 710                 715                 720

Ala Asn Ala Phe Leu Gly Ile Ala His Ser Ile Ala His Lys Ile Gly
                725                 730                 735

Gly Glu Tyr Gly Ile Pro His Gly Arg Ala Asn Ala Ile Leu Leu Pro
                740                 745                 750

His Ile Ile Arg Tyr Asn Ala Lys Asp Pro Gln Lys His Ala Leu Phe
                755                 760                 765

Pro Lys Tyr Glu Phe Phe Arg Ala Asp Thr Asp Tyr Ala Asp Ile Ala
770                 775                 780

Lys Phe Leu Gly Leu Lys Gly Asn Thr Thr Glu Ala Leu Val Glu Ser
785                 790                 795                 800

Leu Ala Lys Ala Val Tyr Glu Leu Gly Gln Ser Val Gly Ile Glu Met
                805                 810                 815

Asn Leu Lys Ser Gln Gly Val Ser Glu Glu Leu Asn Glu Ser Ile
                820                 825                 830

Asp Arg Met Ala Glu Leu Ala Phe Glu Asp Gln Cys Thr Thr Ala Asn
835                 840                 845

Pro Lys Glu Ala Leu Ile Ser Glu Ile Lys Asp Ile Ile Gln Thr Ser
850                 855                 860

Tyr Asp Tyr Lys Gln
865

<210> SEQ ID NO 6
<211> LENGTH: 367
<212> TYPE: PRT
<213> ORGANISM: Escherichia coli
<220> FEATURE:
<221> NAME/KEY: MISC_FEATURE
<222> LOCATION: (1)..(367)
<223> OTHER INFORMATION: E. coli glycerol dehydrogenase (Ec_gldA) amino
      acid sequence

<400> SEQUENCE: 6

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
                20                  25                  30

Leu Val Val Gly Asp Lys Phe Val Leu Gly Phe Ala Gln Ser Thr Val
            35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
                100                 105                 110

Ile Ala Pro Thr Ile Ala Ser Thr Asp Ala Pro Cys Ser Ala Leu Ser
            115                 120                 125

Val Ile Tyr Thr Asp Glu Gly Glu Phe Asp Arg Tyr Leu Leu Leu Pro
130                 135                 140

-continued

```
Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala His Ala Val
                245                 250                 255

His Asn Gly Leu Thr Ala Ile Pro Asp Ala His His Tyr Tyr His Gly
                260                 265                 270

Glu Lys Val Ala Phe Gly Thr Leu Thr Gln Leu Val Leu Glu Asn Ala
            275                 280                 285

Pro Val Glu Glu Ile Glu Thr Val Ala Ala Leu Ser His Ala Val Gly
            290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
                340                 345                 350

Leu Val Ala Asp Gln Tyr Gly Gln Arg Phe Leu Gln Glu Trp Glu
            355                 360                 365
```

<210> SEQ ID NO 7
<211> LENGTH: 365
<212> TYPE: PRT
<213> ORGANISM: Klebsiella pneumoniae
<220> FEATURE:
<221> NAME/KEY: MISC_FEATURE
<222> LOCATION: (1)..(365)
<223> OTHER INFORMATION: K. pneumoniae glycerol dehydrogenase
      (Kpne_gldA) amino acid sequence

<400> SEQUENCE: 7

```
Met Leu Lys Val Ile Gln Ser Pro Ala Lys Tyr Leu Gln Gly Pro Asp
1               5                   10                  15

Ala Ala Val Leu Phe Gly Gln Tyr Ala Lys Asn Leu Ala Glu Ser Phe
                20                  25                  30

Phe Val Ile Ala Asp Asp Phe Val Met Lys Leu Ala Gly Glu Lys Val
            35                  40                  45

Val Asn Gly Leu Gln Ser His Asp Ile Arg Cys His Ala Glu Arg Phe
    50                  55                  60

Asn Gly Glu Cys Ser His Ala Glu Ile Asn Arg Leu Met Ala Ile Leu
65                  70                  75                  80

Gln Lys Gln Gly Cys Arg Gly Val Val Gly Ile Gly Gly Gly Lys Thr
                85                  90                  95

Leu Asp Thr Ala Lys Ala Ile Gly Tyr Tyr Gln Lys Leu Pro Val Val
            100                 105                 110

Val Ile Pro Thr Ile Ala Ser Thr Asp Ala Pro Thr Ser Ala Leu Ser
        115                 120                 125
```

```
Val Ile Tyr Thr Glu Ala Gly Glu Phe Glu Glu Tyr Leu Ile Tyr Pro
        130                 135                 140

Lys Asn Pro Asp Met Val Val Met Asp Thr Ala Ile Ile Ala Lys Ala
145                 150                 155                 160

Pro Val Arg Leu Leu Val Ser Gly Met Gly Asp Ala Leu Ser Thr Trp
                165                 170                 175

Phe Glu Ala Lys Ala Cys Tyr Asp Ala Arg Ala Thr Ser Met Ala Gly
                180                 185                 190

Gly Gln Ser Thr Glu Ala Ala Leu Ser Leu Ala Arg Leu Cys Tyr Asp
            195                 200                 205

Thr Leu Leu Ala Glu Gly Glu Lys Ala Arg Leu Ala Ala Gln Ala Gly
    210                 215                 220

Val Val Thr Glu Ala Leu Glu Arg Ile Ile Glu Ala Asn Thr Tyr Leu
225                 230                 235                 240

Ser Gly Ile Gly Phe Glu Ser Ser Gly Leu Ala Ala His Ala Ile
                245                 250                 255

His Asn Gly Phe Thr Ile Leu Glu Glu Cys His His Leu Tyr His Gly
                260                 265                 270

Glu Lys Val Ala Phe Gly Thr Leu Ala Gln Leu Val Leu Gln Asn Ser
            275                 280                 285

Pro Met Asp Glu Ile Glu Thr Val Leu Gly Phe Cys Gln Arg Val Gly
    290                 295                 300

Leu Pro Val Thr Leu Ala Gln Met Gly Val Lys Glu Gly Ile Asp Ala
305                 310                 315                 320

Lys Ile Ala Ala Val Ala Lys Ala Thr Cys Ala Glu Gly Glu Thr Ile
                325                 330                 335

His Asn Met Pro Phe Ala Val Thr Pro Glu Ser Val His Ala Ala Ile
                340                 345                 350

Leu Thr Ala Asp Leu Leu Gly Gln Gln Trp Leu Ala Arg
            355                 360                 365

<210> SEQ ID NO 8
<211> LENGTH: 367
<212> TYPE: PRT
<213> ORGANISM: Enterococcus aerogenes
<220> FEATURE:
<221> NAME/KEY: MISC_FEATURE
<222> LOCATION: (1)..(367)
<223> OTHER INFORMATION: E. aerogenes glycerol dehydrogenase (Eaer_gldA)
      amino acid sequence

<400> SEQUENCE: 8

Met Asp Arg Ile Ile Gln Ser Pro Gly Lys Tyr Ile Gln Gly Ala Gly
1               5                   10                  15

Ala Ile Lys Arg Leu Gly Glu Tyr Leu Lys Pro Leu Ala Glu Arg Trp
                20                  25                  30

Leu Ile Ile Gly Asp Lys Phe Val Leu Gly Phe Ala Glu Glu Gln Leu
            35                  40                  45

Arg Thr Ser Leu Gly Gly Ala Gly Leu Val Ala Glu Ile Ala Pro Phe
    50                  55                  60

Gly Gly Glu Cys Ser Gln Asn Glu Ile Asn Arg Leu Arg Asp Ile Ala
65                  70                  75                  80

Ser Ser Ala Gln Cys His Ala Val Leu Gly Ile Gly Gly Gly Lys Thr
                85                  90                  95

Leu Asp Thr Ala Lys Ala Leu Ala His Tyr Met His Leu Pro Val Val
                100                 105                 110
```

Val Ala Pro Thr Ile Ala Ser Thr Asp Ala Pro Cys Ser Ala Leu Ser
            115                 120                 125

Val Ile Tyr Thr Asp Asp Gly Glu Phe Glu Ser Tyr Leu Met Leu Pro
        130                 135                 140

His Asn Pro Asn Met Val Val Asp Thr Gln Ile Val Ala Ala Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
                180                 185                 190

Gly Lys Cys Thr Gln Ala Ala Leu Ala Leu Ala Glu Leu Cys Tyr Asn
            195                 200                 205

Thr Leu Val Glu Glu Gly Glu Lys Ala Met Leu Ala Ala Glu Gln His
        210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Leu Ala Ala His Ala Ile
                245                 250                 255

His Asn Gly Leu Thr Ala Ile Pro Asp Ala His His Phe Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Ala Ala Leu Cys His Ser Val Gly
        290                 295                 300

Leu Pro Ile Thr Leu Ala Gln Leu Asp Ile Lys Gly Asp Ile Pro Ala
305                 310                 315                 320

Lys Met Arg Thr Val Ala Glu Ala Ala Cys Ala Glu Gly Glu Thr Ile
                325                 330                 335

His Asn Met Pro Gly Gly Ala Cys Ala Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 9
<211> LENGTH: 364
<212> TYPE: PRT
<213> ORGANISM: Yersinia aldovae
<220> FEATURE:
<221> NAME/KEY: MISC_FEATURE
<222> LOCATION: (1)..(364)
<223> OTHER INFORMATION: Y. aldovae glycerol dehydrogenase (Eaer_gldA)
      amino acid sequence

<400> SEQUENCE: 9

Met Leu Lys Val Ile Gln Ser Pro Ser Lys Tyr Ile Gln Gly Ala Asn
1               5                   10                  15

Ala Leu Gln Ser Ile Gly Glu Phe Ala Lys Leu Leu Ala Asn Asn Tyr
            20                  25                  30

Phe Ile Ile Ala Asp Asp Phe Val Met Lys Leu Thr Ala Asp Thr Val
        35                  40                  45

Gly Thr Ser Leu Gln Thr Cys Glu Leu Lys Ser His Phe Ser Arg Phe
    50                  55                  60

Asn Gly Glu Cys Ser Arg Gln Glu Ile Glu Arg Leu Thr Val Glu Leu
65                  70                  75                  80

Lys Lys Tyr Gly Cys Asn Gly Val Ile Gly Ile Gly Gly Gly Lys Thr
                85                  90                  95

```
Leu Asp Thr Ala Lys Ala Ile Ala His Tyr Gln His Ile Pro Val Val
                100                 105                 110

Val Val Pro Thr Ile Ala Ser Thr Asp Ala Pro Thr Ser Ala Leu Ser
            115                 120                 125

Val Ile Tyr Thr Glu Gln Gly Glu Phe Ala Glu Tyr Leu Ile Tyr Pro
        130                 135                 140

Lys Asn Pro Asp Ile Val Leu Met Asp Thr Thr Ile Ile Ala Lys Ala
145                 150                 155                 160

Pro Val Arg Leu Leu Val Ala Gly Met Gly Asp Ala Leu Ser Thr Tyr
                165                 170                 175

Phe Glu Ala Gln Ala Cys Phe Asp Ala Lys Ala Ile Ser Met Ala Gly
            180                 185                 190

Gly Ala Ser Thr Leu Ala Ala Ile Thr Leu Ala Arg Leu Cys Tyr Glu
        195                 200                 205

Thr Leu Leu Ala Glu Gly Tyr Lys Ala Lys Leu Ala Val Glu Ala Gly
    210                 215                 220

Val Val Thr Glu Ala Val Glu Arg Ile Ile Glu Ala Asn Thr Tyr Leu
225                 230                 235                 240

Ser Gly Ile Gly Phe Glu Ser Ser Gly Leu Ala Ala His Ala Ile
                245                 250                 255

His Asn Gly Phe Thr Val Leu Glu Glu Cys His His Leu Tyr His Gly
            260                 265                 270

Glu Lys Val Ala Phe Gly Thr Leu Thr Gln Leu Val Leu Gln Asn Ser
        275                 280                 285

Ser Met Glu Glu Ile Glu Thr Val Leu Ser Phe Cys Gln Gln Leu Gly
    290                 295                 300

Leu Pro Ile Thr Leu Ala Glu Met Gly Val Thr Gln Asp Leu Glu Cys
305                 310                 315                 320

Lys Ile Arg Ala Val Ala Gln Ala Ser Cys Ala Glu Gly Glu Thr Ile
                325                 330                 335

His Asn Met Pro Phe Lys Val Thr Ala Asp Ser Val Tyr Ala Ala Ile
            340                 345                 350

Ile Val Ala Asp Arg Leu Gly Gln Ala Phe Leu Asn
        355                 360

<210> SEQ ID NO 10
<211> LENGTH: 584
<212> TYPE: PRT
<213> ORGANISM: Saccharomyces cerevisiae
<220> FEATURE:
<221> NAME/KEY: MISC_FEATURE
<222> LOCATION: (1)..(584)
<223> OTHER INFORMATION: S. cerevisiae dihydroxyacetone kinase (S.
      cerevisiae DAK1) amino acid sequence

<400> SEQUENCE: 10

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80
```

```
Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
            115                 120                 125

Ala Val Ile Gly Asp Asp Val Ala Val Gly Arg Glu Lys Gly Gly Met
130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
            195                 200                 205

Asn Glu Lys Gln Met Glu Leu Gly Met Gly Ile His Asn Glu Pro Gly
210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
            260                 265                 270

Gly Gly Val Ser Asn Phe Val Ile Ser Ser Ile Thr Ser Lys Thr Thr
            275                 280                 285

Asp Phe Leu Lys Glu Asn Tyr Asn Ile Thr Pro Val Gln Thr Ile Ala
290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
            355                 360                 365

Asp Leu Leu His Asn Glu Val Thr Ala Lys Ala Val Gly Thr Tyr Asp
370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
            435                 440                 445

Ser Asp Phe Ile Glu Gly Ser Met Gly Gly Thr Ser Gly Gly Leu Tyr
450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495
```

```
Ile Ala Leu Asp Thr Leu Tyr Lys Tyr Thr Lys Ala Arg Lys Gly Ser
                500                 505                 510

Ser Thr Met Ile Asp Ala Leu Glu Pro Phe Val Lys Glu Phe Thr Ala
            515                 520                 525

Ser Lys Asp Phe Asn Lys Ala Val Lys Ala Ala Glu Glu Gly Ala Lys
        530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575

Leu Lys Gly Val Gln Ser Ala Leu
            580

<210> SEQ ID NO 11
<211> LENGTH: 572
<212> TYPE: PRT
<213> ORGANISM: Klebsiella pneumoniae
<220> FEATURE:
<221> NAME/KEY: MISC_FEATURE
<222> LOCATION: (1)..(572)
<223> OTHER INFORMATION: K. pneumoniae dihydroxyacetone kinase
      (Kpne_dhaK) amino acid sequence

<400> SEQUENCE: 11

Met Thr Thr Lys Gln Phe Gln Phe Asp Ser Asp Pro Leu Asn Ser Ala
1               5                   10                  15

Leu Ala Ala Thr Ala Glu Ala Ser Gly Leu Ala Tyr Leu Pro Lys Ser
            20                  25                  30

Lys Val Ile Tyr Tyr Pro Leu Thr Asn Asp Lys Val Thr Leu Ile Ser
        35                  40                  45

Gly Gly Gly Ala Gly His Glu Pro Ala Gln Thr Gly Phe Val Gly Pro
    50                  55                  60

Gly Leu Leu Asp Ala Ala Val Ser Gly Gln Ile Phe Ala Ser Pro Ser
65                  70                  75                  80

Thr Lys Gln Ile Ile Ala Gly Val Asn Ala Val Lys Ser Gln Arg Gly
                85                  90                  95

Ser Ile Ile Ile Val Met Asn Tyr Thr Gly Asp Val Ile His Phe Gly
            100                 105                 110

Met Ala Ala Glu Gln Leu Arg Ser Arg Tyr Asp Tyr His Ala Glu Leu
        115                 120                 125

Val Ser Ile Gly Asp Asp Ile Ser Val Asn Lys Lys Ala Gly Arg Arg
    130                 135                 140

Gly Leu Ala Gly Thr Val Leu Val His Lys Ile Ala Gly His Leu Ala
145                 150                 155                 160

Arg Asp Gly Trp Asp Val Gly Val Leu Ala Glu Ala Leu Arg Thr Thr
                165                 170                 175

Ala Ala Asn Leu Ala Thr Val Ala Ala Ser Leu Glu His Cys Thr Val
            180                 185                 190

Pro Gly Arg Lys Phe Glu Thr Glu Leu Ala Ala Asp Glu Met Glu Ile
        195                 200                 205

Gly Met Gly Ile His Asn Glu Pro Gly Val Lys Thr Ile Lys Ile Gly
    210                 215                 220

Lys Val Glu Ser Leu Leu Asp Glu Leu Val Asp Lys Phe Glu Pro Ser
225                 230                 235                 240

Lys Gln Asp Phe Val Pro Phe Asn Lys Gly Asp Glu Val Val Leu Leu
                245                 250                 255
```

```
Val Asn Ser Leu Gly Gly Val Ser Ser Leu Glu Leu His Ala Ile Ala
            260                 265                 270

Asn Ile Ala Gln Thr Lys Phe Glu Lys Val Leu Gly Val Lys Thr Val
        275                 280                 285

Arg Leu Ile Val Gly Asn Phe Met Ala Phe Asn Gly Pro Gly Phe
    290                 295                 300

Ser Leu Thr Leu Leu Asn Val Thr Thr Ala Lys Lys Gly Asn Phe
305                 310                 315                 320

Asp Val Leu Gly Ala Leu Asp Ala Pro Val Ser Thr Ala Ala Trp Pro
                325                 330                 335

Ser Leu Gln Gln Lys Asp Lys Pro Ala Asn Gly Gly Val Gln Glu Glu
            340                 345                 350

Lys Glu Thr Asp Ser Asp Lys Pro Ala Glu Pro Thr Gly Ile Lys Ala
            355                 360                 365

Asp Gly Lys Leu Phe Lys Ala Met Ile Glu Ser Ala Val Asp Asp Leu
    370                 375                 380

Lys Lys Glu Glu Pro Gln Ile Thr Lys Tyr Asp Thr Ile Ala Gly Asp
385                 390                 395                 400

Gly Asp Cys Gly Glu Thr Leu Leu Ala Gly Gly Asp Gly Ile Leu Asp
                405                 410                 415

Ala Ile Lys Asn Lys Lys Ile Asp Leu Asp Asp Ala Ala Gly Val Ala
                420                 425                 430

Asp Ile Ser His Ile Val Glu Asn Ser Met Gly Gly Thr Ser Gly Gly
            435                 440                 445

Leu Tyr Ser Ile Phe Phe Ser Gly Leu Val Val Gly Ile Lys Glu Thr
    450                 455                 460

Lys Ala Lys Glu Leu Ser Val Asp Val Phe Ala Lys Ala Cys Glu Thr
465                 470                 475                 480

Ala Leu Glu Thr Leu Ser Lys Tyr Thr Gln Ala Arg Val Gly Asp Arg
                485                 490                 495

Thr Leu Met Asp Ala Leu Val Pro Phe Val Glu Thr Leu Ser Lys Thr
            500                 505                 510

Lys Asp Phe Ala Lys Ala Val Glu Ala Ala Arg Lys Gly Ala Asp Glu
        515                 520                 525

Thr Ser Lys Leu Pro Ala Asn Phe Gly Arg Ala Ser Tyr Val Asn Glu
530                 535                 540

Glu Gly Leu Glu Asn Ile Pro Asp Pro Gly Ala Leu Gly Leu Ala Val
545                 550                 555                 560

Ile Phe Glu Gly Leu Leu Lys Ala Trp Glu Lys Lys
                565                 570

<210> SEQ ID NO 12
<211> LENGTH: 580
<212> TYPE: PRT
<213> ORGANISM: Yarrowia lipolytica
<220> FEATURE:
<221> NAME/KEY: MISC_FEATURE
<222> LOCATION: (1)..(580)
<223> OTHER INFORMATION: Y. lipolytica dihydroxyacetone kinase
      (Ylip_DAK1) amino acid sequence

<400> SEQUENCE: 12

Met Asp Lys His Phe Ile Asn Asp Pro Glu Val Leu Val Leu Asp Gly
1               5                   10                  15

Leu Lys Ser Leu Ala Asp Met Asn Lys Thr Leu Thr Val His Glu Glu
            20                  25                  30
```

```
Gly Lys Phe Ile Tyr Phe His Asp Tyr Asn Lys Lys Asn Val Ser Val
         35                  40                  45

Ile Ser Gly Gly Gly Ala Gly His Glu Pro Thr His Ser Ser Phe Val
 50                  55                  60

Gly Lys Gly Met Leu Thr Ala Ala Val Ser Gly Ser Ile Phe Ala Ser
 65                  70                  75                  80

Pro Ser Ser Lys Gln Ile Tyr Thr Gly Ile Lys Gln Val Glu Ser Glu
                 85                  90                  95

Ala Gly Thr Leu Val Ile Cys Lys Asn Tyr Thr Gly Asp Ile Leu His
                100                 105                 110

Phe Gly Met Ala Leu Glu Lys Gln Arg Thr Ala Gly Lys Lys Ala Glu
            115                 120                 125

Leu Ile Ala Val Ala Asp Asp Val Ser Val Gly Arg Lys Lys Ser Gly
130                 135                 140

Lys Val Gly Arg Arg Gly Leu Ser Gly Thr Val Leu Val His Lys Ile
145                 150                 155                 160

Ala Gly Ala Ala Ala Ala Arg Gly Leu Pro Leu Glu Ala Val Thr Thr
                165                 170                 175

Ile Ala Lys Ala Ala Ile Asp Asn Leu Val Ser Ile Gly Ala Ser Leu
            180                 185                 190

Ala His Val His Val Pro Gly His Glu Pro Ile Ala Lys Glu Asp Glu
        195                 200                 205

Met Lys His Asp Glu Met Glu Leu Gly Met Gly Ile His Asn Glu Pro
210                 215                 220

Gly Cys Lys Arg Ile Ser Pro Ile Pro Ser Ile Asp Asp Leu Ile Ala
225                 230                 235                 240

Gln Met Leu Lys Gln Met Leu Asp Gln Ser Asp Lys Asp Arg Ala Tyr
                245                 250                 255

Val Lys Ile Glu Gly Asp Asp Glu Val Val Leu Leu Met Asn Asn Leu
            260                 265                 270

Gly Gly Leu Ser Met Leu Glu Phe Ser Ala Ile Ser His Lys Val Lys
        275                 280                 285

Glu Ala Leu Ala Lys Glu Tyr Lys Ile Asn Pro Val Arg Ile Phe Ala
290                 295                 300

Gly Pro Phe Thr Thr Ser Leu Asn Gly Leu Gly Phe Gly Ile Thr Leu
305                 310                 315                 320

Leu Arg Thr Thr Asp Arg Val Lys Val Glu Gly Glu Glu Tyr Ser Leu
                325                 330                 335

Val Asp Leu Ile Asp Gln Pro Val Glu Ala Ile Gly Trp Pro Leu Cys
            340                 345                 350

Gln Pro Ser Asp Leu Lys Ser Lys Asn Lys Ile Gly Asn Val Ser Ile
        355                 360                 365

Glu Glu Gly Gln Lys Asp Val Lys Ser Pro Val Thr Val Asp Lys Glu
370                 375                 380

Lys Val Arg Gln Ala Ile Val Asn Ser Met Glu Asn Leu Ile Lys Ala
385                 390                 395                 400

Glu Pro Lys Ile Thr Lys Phe Asp Thr Met Ala Gly Asp Gly Asp Cys
                405                 410                 415

Gly Thr Thr Leu Lys Arg Gly Ala Glu Gly Val Leu Lys Phe Val Lys
            420                 425                 430

Ser Asp Lys Phe Ser Asp Asp Pro Ile Arg Ile Val Arg Asp Ile Ala
        435                 440                 445
```

```
Asp Val Ile Glu Asp Asn Met Asp Gly Thr Ser Gly Ala Leu Tyr Ala
    450                 455                 460

Ile Phe Phe His Gly Phe Ala Lys Gly Met Lys Asp Thr Leu Glu Lys
465                 470                 475                 480

Ser Lys Asp Ile Ser Ser Lys Thr Trp Ala Ala Gly Leu Lys Val Ala
                485                 490                 495

Leu Asp Thr Leu Phe Lys Tyr Thr Pro Ala Arg Pro Gly Asp Ser Thr
                500                 505                 510

Met Cys Asp Ala Leu Val Pro Phe Val Glu Thr Phe Val Lys Thr Asn
                515                 520                 525

Asp Leu Asn Ala Ala Val Glu Glu Ala Arg Lys Gly Ala Asp Ala Thr
530                 535                 540

Ala Asp Met Gln Ala Lys Leu Gly Arg Ala Val Tyr Val Gly Asp Asp
545                 550                 555                 560

Val Lys Val Pro Asp Ala Gly Ala Leu Gly Val Val Ala Ile Val Glu
                565                 570                 575

Gly Phe Thr Lys
            580

<210> SEQ ID NO 13
<211> LENGTH: 580
<212> TYPE: PRT
<213> ORGANISM: Schizosaccharomyces pombe
<220> FEATURE:
<221> NAME/KEY: MISC_FEATURE
<222> LOCATION: (1)..(580)
<223> OTHER INFORMATION: S. pombe dihydroxyacetone kinase (Spom_DAK1)
      amino acid sequence

<400> SEQUENCE: 13

Met Asp Lys His Phe Ile Asn Asp Pro Glu Val Leu Val Leu Asp Gly
1               5                   10                  15

Leu Lys Ser Leu Ala Asp Met Asn Lys Thr Leu Thr Val His Glu Glu
                20                  25                  30

Gly Lys Phe Ile Tyr Phe His Asp Tyr Asn Lys Lys Asn Val Ser Val
            35                  40                  45

Ile Ser Gly Gly Gly Ala Gly His Glu Pro Thr His Ser Ser Phe Val
50                  55                  60

Gly Lys Gly Met Leu Thr Ala Ala Val Ser Gly Ser Ile Phe Ala Ser
65                  70                  75                  80

Pro Ser Ser Lys Gln Ile Tyr Thr Gly Ile Lys Gln Val Glu Ser Glu
                85                  90                  95

Ala Gly Thr Leu Val Ile Cys Lys Asn Tyr Thr Gly Asp Ile Leu His
            100                 105                 110

Phe Gly Met Ala Leu Glu Lys Gln Arg Thr Ala Gly Lys Lys Ala Glu
        115                 120                 125

Leu Ile Ala Val Ala Asp Asp Val Ser Val Gly Arg Lys Lys Ser Gly
130                 135                 140

Lys Val Gly Arg Arg Gly Leu Ser Gly Thr Val Leu Val His Lys Ile
145                 150                 155                 160

Ala Gly Ala Ala Ala Ala Arg Gly Leu Pro Leu Glu Ala Val Thr Thr
                165                 170                 175

Ile Ala Lys Ala Ala Ile Asp Asn Leu Val Ser Ile Gly Ala Ser Leu
            180                 185                 190

Ala His Val His Val Pro Gly His Glu Pro Ile Ala Lys Glu Asp Glu
        195                 200                 205
```

Met Lys His Asp Glu Met Glu Leu Gly Met Gly Ile His Asn Glu Pro
210                 215                 220

Gly Cys Lys Arg Ile Ser Pro Ile Pro Ser Ile Asp Asp Leu Ile Ala
225                 230                 235                 240

Gln Met Leu Lys Gln Met Leu Asp Gln Ser Asp Lys Asp Arg Ala Tyr
            245                 250                 255

Val Lys Ile Glu Gly Asp Asp Glu Val Val Leu Leu Met Asn Asn Leu
        260                 265                 270

Gly Gly Leu Ser Met Leu Glu Phe Ser Ala Ile Ser His Lys Val Lys
    275                 280                 285

Glu Ala Leu Ala Lys Glu Tyr Lys Ile Asn Pro Val Arg Ile Phe Ala
290                 295                 300

Gly Pro Phe Thr Thr Ser Leu Asn Gly Leu Gly Phe Gly Ile Thr Leu
305                 310                 315                 320

Leu Arg Thr Thr Asp Arg Val Lys Val Glu Gly Glu Tyr Ser Leu
            325                 330                 335

Val Asp Leu Ile Asp Gln Pro Val Glu Ala Ile Gly Trp Pro Leu Cys
        340                 345                 350

Gln Pro Ser Asp Leu Lys Ser Lys Asn Lys Ile Gly Asn Val Ser Ile
    355                 360                 365

Glu Glu Gly Gln Lys Asp Val Lys Ser Pro Val Thr Val Asp Lys Glu
370                 375                 380

Lys Val Arg Gln Ala Ile Val Asn Ser Met Glu Asn Leu Ile Lys Ala
385                 390                 395                 400

Glu Pro Lys Ile Thr Lys Phe Asp Thr Met Ala Gly Asp Gly Asp Cys
            405                 410                 415

Gly Thr Thr Leu Lys Arg Gly Ala Glu Gly Val Leu Lys Phe Val Lys
        420                 425                 430

Ser Asp Lys Phe Ser Asp Asp Pro Ile Arg Ile Val Arg Asp Ile Ala
    435                 440                 445

Asp Val Ile Glu Asp Asn Met Asp Gly Thr Ser Gly Ala Leu Tyr Ala
450                 455                 460

Ile Phe Phe His Gly Phe Ala Lys Gly Met Lys Asp Thr Leu Glu Lys
465                 470                 475                 480

Ser Lys Asp Ile Ser Ser Lys Thr Trp Ala Ala Gly Leu Lys Val Ala
            485                 490                 495

Leu Asp Thr Leu Phe Lys Tyr Thr Pro Ala Arg Pro Gly Asp Ser Thr
        500                 505                 510

Met Cys Asp Ala Leu Val Pro Phe Val Glu Thr Phe Val Lys Thr Asn
    515                 520                 525

Asp Leu Asn Ala Ala Val Glu Glu Ala Arg Lys Gly Ala Asp Ala Thr
530                 535                 540

Ala Asp Met Gln Ala Lys Leu Gly Arg Ala Val Tyr Val Gly Asp Asp
545                 550                 555                 560

Val Lys Val Pro Asp Ala Gly Ala Leu Gly Val Val Ala Ile Val Glu
            565                 570                 575

Gly Phe Thr Lys
            580

<210> SEQ ID NO 14
<211> LENGTH: 291
<212> TYPE: PRT
<213> ORGANISM: Danio rerio
<220> FEATURE:

-continued

<221> NAME/KEY: MISC_FEATURE
<222> LOCATION: (1)..(291)
<223> OTHER INFORMATION: D. rerio aquaporin 9 (Drer_T3) amino acid
      sequence

<400> SEQUENCE: 14

Met Glu Tyr Leu Glu Asn Ile Arg Asn Leu Arg Gly Arg Cys Val Leu
1               5                   10                  15

Arg Arg Asp Ile Ile Arg Glu Phe Leu Ala Glu Leu Leu Gly Thr Phe
            20                  25                  30

Val Leu Ile Leu Phe Gly Cys Gly Ser Val Ala Gln Thr Val Leu Ser
        35                  40                  45

Arg Glu Ala Lys Gly Gln Leu Leu Thr Ile His Phe Gly Phe Thr Leu
    50                  55                  60

Gly Val Met Leu Ala Val Tyr Met Ala Gly Gly Val Ser Gly Gly His
65                  70                  75                  80

Val Asn Pro Ala Val Ser Leu Ala Met Val Val Leu Arg Lys Leu Pro
                85                  90                  95

Leu Lys Lys Phe Pro Val Tyr Val Leu Ala Gln Phe Leu Gly Ala Phe
            100                 105                 110

Phe Gly Ser Cys Ala Val Tyr Cys Leu Tyr Tyr Asp Ala Phe Thr Glu
        115                 120                 125

Phe Ala Asn Gly Glu Leu Ala Val Thr Gly Pro Asn Val Thr Ala Gly
    130                 135                 140

Ile Phe Ala Ser Tyr Pro Arg Glu Gly Leu Ser Leu Leu Asn Gly Phe
145                 150                 155                 160

Ile Asp Gln Val Ile Gly Ala Gly Ala Leu Val Leu Cys Ile Leu Ala
                165                 170                 175

Val Val Asp Lys Lys Asn Ile Gly Ala Pro Lys Gly Met Glu Pro Leu
            180                 185                 190

Leu Val Gly Leu Ser Ile Leu Ala Ile Gly Val Ser Met Ala Leu Asn
        195                 200                 205

Cys Gly Tyr Pro Ile Asn Pro Ala Arg Asp Leu Gly Pro Arg Leu Phe
    210                 215                 220

Thr Ala Ile Ala Gly Trp Gly Leu Thr Val Phe Ser Ala Gly Asn Gly
225                 230                 235                 240

Trp Trp Trp Val Pro Val Val Gly Pro Met Val Gly Gly Val Val Gly
                245                 250                 255

Ala Ala Ile Tyr Phe Leu Met Ile Glu Met His His Pro Glu Asn Asp
            260                 265                 270

Lys Asn Leu Glu Asp Asp Asn Ser Leu Lys Asp Lys Tyr Glu Leu Asn
        275                 280                 285

Thr Val Asn
    290

<210> SEQ ID NO 15
<211> LENGTH: 592
<212> TYPE: PRT
<213> ORGANISM: Zygosaccharomyces rouxii
<220> FEATURE:
<221> NAME/KEY: MISC_FEATURE
<222> LOCATION: (1)..(592)
<223> OTHER INFORMATION: Z. rouxii ZYRO0E01210p (Zrou_T5) amino acid
      sequence

<400> SEQUENCE: 15

Met Gly Lys Arg Thr Gln Gly Phe Met Asp Tyr Val Phe Ser Arg Thr
1               5                   10                  15

```
Ser Thr Ala Gly Leu Lys Gly Ala Arg Leu Arg Tyr Thr Ala Ala Ala
         20                  25                  30

Val Ala Val Ile Gly Phe Ala Leu Phe Gly Tyr Asp Gln Gly Leu Met
             35                  40                  45

Ser Gly Leu Ile Thr Gly Asp Gln Phe Asn Lys Glu Phe Pro Pro Thr
 50                  55                  60

Lys Ser Asn Gly Asp Asn Asp Arg Tyr Ala Ser Val Ile Gln Gly Ala
 65                  70                  75                  80

Val Thr Ala Cys Tyr Glu Ile Gly Cys Phe Phe Gly Ser Leu Phe Val
                 85                  90                  95

Leu Phe Phe Gly Asp Ala Ile Gly Arg Lys Pro Leu Ile Ile Phe Gly
                100                 105                 110

Ala Ile Ile Val Ile Ile Gly Thr Val Ile Ser Thr Ala Pro Phe His
                115                 120                 125

His Ala Trp Gly Leu Gly Gln Phe Val Val Gly Arg Val Ile Thr Gly
    130                 135                 140

Val Gly Thr Gly Phe Asn Thr Ser Thr Ile Pro Val Trp Gln Ser Glu
145                 150                 155                 160

Met Thr Lys Pro Asn Ile Arg Gly Ala Met Ile Asn Leu Asp Gly Ser
                165                 170                 175

Val Ile Ala Phe Gly Thr Met Ile Ala Tyr Trp Leu Asp Phe Gly Phe
                180                 185                 190

Ser Phe Ile Asn Ser Ser Val Gln Trp Arg Phe Pro Val Ser Val Gln
        195                 200                 205

Ile Ile Phe Ala Leu Val Leu Leu Phe Gly Ile Val Arg Met Pro Glu
    210                 215                 220

Ser Pro Arg Trp Leu Met Ala Lys Lys Arg Pro Ala Glu Ala Arg Tyr
225                 230                 235                 240

Val Leu Ala Cys Leu Asn Asp Leu Pro Glu Asn Asp Asp Ala Ile Leu
                245                 250                 255

Ala Glu Met Thr Ser Leu His Glu Ala Val Asn Arg Ser Ser Asn Gln
                260                 265                 270

Lys Ser Gln Met Lys Ser Leu Phe Ser Met Gly Lys Gln Gln Asn Phe
            275                 280                 285

Ser Arg Ala Leu Ile Ala Ser Ser Thr Gln Phe Phe Gln Gln Phe Thr
    290                 295                 300

Gly Cys Asn Ala Ala Ile Tyr Tyr Ser Thr Val Leu Phe Gln Thr Thr
305                 310                 315                 320

Val Gln Leu Asp Arg Leu Leu Ala Met Ile Leu Gly Gly Val Phe Ala
                325                 330                 335

Thr Val Tyr Thr Leu Ser Thr Leu Pro Ser Phe Tyr Leu Val Glu Lys
            340                 345                 350

Val Gly Arg Arg Lys Met Phe Phe Gly Ala Leu Gly Gln Gly Ile
    355                 360                 365

Ser Phe Ile Ile Thr Phe Ala Cys Leu Val Asn Pro Thr Lys Gln Asn
    370                 375                 380

Ala Lys Gly Ala Ala Val Gly Leu Tyr Leu Phe Ile Ile Cys Phe Gly
385                 390                 395                 400

Leu Ala Ile Leu Glu Leu Pro Trp Ile Tyr Pro Pro Glu Ile Ala Ser
                405                 410                 415

Met Arg Val Arg Ala Ala Thr Asn Ala Met Ser Thr Cys Thr Asn Trp
                420                 425                 430
```

```
Val Thr Asn Phe Ala Val Val Met Phe Thr Pro Val Phe Ile Gln Thr
            435                 440                 445

Ser Gln Trp Gly Cys Tyr Leu Phe Phe Ala Val Met Asn Phe Ile Tyr
        450                 455                 460

Leu Pro Val Ile Phe Phe Tyr Pro Glu Thr Ala Gly Arg Ser Leu
465                 470                 475                 480

Glu Glu Ile Asp Ile Ile Phe Ala Lys Ala His Val Asp Gly Thr Leu
                485                 490                 495

Pro Trp Met Val Ala His Arg Leu Pro Lys Leu Ser Met Thr Glu Val
                500                 505                 510

Glu Asp Tyr Ser Gln Ser Leu Gly Leu His Asp Asp Glu Asn Glu Lys
            515                 520                 525

Glu Glu Tyr Asp Glu Lys Glu Ala Glu Ala Asn Ala Ala Leu Phe Gln
        530                 535                 540

Val Glu Thr Ser Ser Lys Ser Pro Ser Ser Asn Arg Lys Asp Asp Asp
545                 550                 555                 560

Ala Pro Ile Glu His Asn Glu Val Gln Glu Ser Asn Asp Asn Ser Ser
                565                 570                 575

Asn Ser Ser Asn Val Glu Ala Pro Ile Pro Val His His Asn Asp Pro
            580                 585                 590

<210> SEQ ID NO 16
<211> LENGTH: 825
<212> TYPE: PRT
<213> ORGANISM: Bifidobacterium animalis
<220> FEATURE:
<221> NAME/KEY: MISC_FEATURE
<222> LOCATION: (1)..(825)
<223> OTHER INFORMATION: B. animalis xylulose-5P/fructose-6P
      phosphoketolase (Bani_XFP.orf) amino acid sequence

<400> SEQUENCE: 16

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Asn Thr Val Phe Ile Met Gly Pro Gly
                85                  90                  95

His Gly Gly Pro Ala Gly Thr Ala Gln Ser Tyr Ile Asp Gly Thr Tyr
                100                 105                 110

Thr Glu Tyr Tyr Pro Asn Ile Thr Lys Asp Glu Ala Gly Leu Gln Lys
            115                 120                 125

Phe Phe Arg Gln Phe Ser Tyr Pro Gly Gly Ile Pro Ser His Phe Ala
        130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
                180                 185                 190
```

```
Gly Trp Gln Ser Asn Lys Leu Val Asn Pro Arg Thr Asp Gly Ile Val
            195                 200                 205

Leu Pro Ile Leu His Leu Asn Gly Tyr Lys Ile Ala Asn Pro Thr Ile
210                 215                 220

Leu Ala Arg Ile Ser Asp Glu Glu Leu His Asp Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Gln Thr Asp Asp Met Thr Arg
        275                 280                 285

Pro Phe Tyr Pro Met Leu Ile Phe Arg Thr Pro Lys Gly Trp Thr Cys
290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Glu Asp Val Thr Ala Phe Met Pro Lys Gly Glu
        355                 360                 365

Leu Arg Ile Gly Ala Asn Pro Asn Ala Asn Gly Gly Arg Ile Arg Glu
370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Thr Phe Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
        595                 600                 605
```

Ala Thr Trp Ile Thr Leu Asp Glu Val Arg Ala Glu Leu Glu Ala Gly
610                 615                 620

Ala Ala Glu Trp Lys Trp Ala Ser Asn Ala Lys Ser Asn Asp Glu Val
625                 630                 635                 640

Gln Val Val Leu Ala Ala Gly Asp Val Pro Thr Gln Glu Ile Met
            645                 650                 655

Ala Ala Ser Asp Ala Leu Asn Lys Met Gly Ile Lys Phe Lys Val Val
            660                 665                 670

Asn Val Val Asp Leu Ile Lys Leu Gln Ser Ser Lys Glu Asn Asp Glu
        675                 680                 685

Ala Met Ser Asp Glu Asp Phe Ala Asp Leu Phe Thr Ala Asp Lys Pro
690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
                725                 730                 735

Gln Gly Ser Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
        755                 760                 765

Lys Tyr Ala Asp Lys Ile Asn Glu Leu Asn Glu Phe Arg Lys Thr Ala
770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Ala Thr Ala Gly Asp Asn Glu
            820                 825

<210> SEQ ID NO 17
<211> LENGTH: 825
<212> TYPE: PRT
<213> ORGANISM: Bifidobacterium adolescentis
<220> FEATURE:
<221> NAME/KEY: MISC_FEATURE
<222> LOCATION: (1)..(825)
<223> OTHER INFORMATION: B. adolescentis xylulose-5P/fructose-6P
      phosphoketolase (Bado_XFP.orf) amino acid sequence

<400> SEQUENCE: 17

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Met Gly Pro Gly
            85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

```
Phe Phe Arg Gln Phe Ser Tyr Pro Gly Gly Ile Pro Ser His Tyr Ala
    130                 135                 140
Pro Glu Thr Pro Gly Ser Ile His Glu Gly Gly Glu Leu Gly Tyr Ala
145                 150                 155                 160
Leu Ser His Ala Tyr Gly Ala Val Met Asn Asn Pro Ser Leu Phe Val
                165                 170                 175
Pro Ala Ile Val Gly Asp Gly Glu Ala Glu Thr Gly Pro Leu Ala Thr
            180                 185                 190
Gly Trp Gln Ser Asn Lys Leu Ile Asn Pro Arg Thr Asp Gly Ile Val
        195                 200                 205
Leu Pro Ile Leu His Leu Asn Gly Tyr Lys Ile Ala Asn Pro Thr Ile
210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asn Glu Asp His
                245                 250                 255
Leu Ser Ile His Arg Arg Phe Ala Glu Leu Phe Glu Thr Val Phe Asp
            260                 265                 270
Glu Ile Cys Asp Ile Lys Ala Ala Ala Gln Thr Asp Asp Met Thr Arg
        275                 280                 285
Pro Phe Tyr Pro Met Ile Ile Phe Arg Thr Pro Lys Gly Trp Thr Cys
290                 295                 300
Pro Lys Phe Ile Asp Gly Lys Lys Thr Glu Gly Ser Trp Arg Ser His
305                 310                 315                 320
Gln Val Pro Leu Ala Ser Ala Arg Asp Thr Glu Ala His Phe Glu Val
                325                 330                 335
Leu Lys Asn Trp Leu Glu Ser Tyr Lys Pro Glu Glu Leu Phe Asp Glu
            340                 345                 350
Asn Gly Ala Val Lys Pro Glu Val Thr Ala Phe Met Pro Thr Gly Glu
        355                 360                 365
Leu Arg Ile Gly Glu Asn Pro Asn Ala Asn Gly Gly Arg Ile Arg Glu
370                 375                 380
Glu Leu Lys Leu Pro Lys Leu Glu Asp Tyr Glu Val Lys Glu Val Ala
385                 390                 395                 400
Glu Tyr Gly His Gly Trp Gly Gln Leu Glu Ala Thr Arg Arg Leu Gly
                405                 410                 415
Val Tyr Thr Arg Asp Ile Ile Lys Asn Asn Pro Asp Ser Phe Arg Ile
            420                 425                 430
Phe Gly Pro Asp Glu Thr Ala Ser Asn Arg Leu Gln Ala Ala Tyr Asp
        435                 440                 445
Val Thr Asn Lys Gln Trp Asp Ala Gly Tyr Leu Ser Ala Gln Val Asp
450                 455                 460
Glu His Met Ala Val Thr Gly Gln Val Thr Glu Gln Leu Ser Glu His
465                 470                 475                 480
Gln Met Glu Gly Phe Leu Glu Gly Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ser Ser Met Asn Leu Leu Val Ser Ser His Val Trp
530                 535                 540
```

```
Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
            565                 570                 575

Phe Pro Val Asp Ser Asn Met Leu Leu Ala Val Ala Glu Lys Cys Tyr
        580                 585                 590

Lys Ser Thr Asn Lys Ile Asn Ala Ile Ile Ala Gly Lys Gln Pro Ala
    595                 600                 605

Ala Thr Trp Leu Thr Leu Asp Glu Ala Arg Ala Glu Leu Glu Lys Gly
610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Ala Lys Glu Asn Asn Glu
        675                 680                 685

Ala Leu Ser Asp Glu Glu Phe Ala Glu Leu Phe Thr Glu Asp Lys Pro
    690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Thr Pro Tyr Asp Met Val Arg Val Asn Asn Ile
            740                 745                 750

Asp Arg Tyr Glu Leu Gln Ala Glu Ala Leu Arg Met Ile Asp Ala Asp
        755                 760                 765

Lys Tyr Ala Asp Lys Ile Asn Glu Leu Glu Ala Phe Arg Gln Glu Ala
    770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
                805                 810                 815

Thr Ala Thr Ala Gly Asp Asn Glu
            820                 825

<210> SEQ ID NO 18
<211> LENGTH: 825
<212> TYPE: PRT
<213> ORGANISM: Bifidobacterium lactis
<220> FEATURE:
<221> NAME/KEY: MISC_FEATURE
<222> LOCATION: (1)..(825)
<223> OTHER INFORMATION: B. lactis xylulose-5P/fructose-6P
      phosphoketolase (Blac_XFP.orf) amino acid sequence

<400> SEQUENCE: 18

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60
```

```
Trp Gly Thr Thr Pro Gly Leu Asn Phe Leu Leu Ala His Ile Asn Arg
 65                  70                  75                  80

Leu Ile Ala Asp His Gln Gln Asn Thr Val Phe Ile Met Gly Pro Gly
                 85                  90                  95

His Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
                180                 185                 190

Gly Trp Gln Ser Asn Lys Leu Val Asn Pro Arg Thr Asp Gly Ile Val
            195                 200                 205

Leu Pro Ile Leu His Leu Asn Gly Tyr Lys Ile Ala Asn Pro Thr Ile
210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
            275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Glu Asp Val Thr Ala Phe Met Pro Lys Gly Glu
            355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480
```

Gln Cys Glu Gly Phe Leu Glu Ala Tyr Leu Leu Thr Gly Arg His Gly
            485                 490                 495

Ile Trp Ser Ser Tyr Glu Ser Phe Val His Val Ile Asp Ser Met Leu
        500                 505                 510

Asn Gln His Ala Lys Trp Leu Glu Ala Thr Val Arg Glu Ile Pro Trp
    515                 520                 525

Arg Lys Pro Ile Ser Ser Val Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
        595                 600                 605

Ala Thr Trp Ile Thr Leu Asp Glu Ala Arg Ala Glu Leu Glu Ala Gly
    610                 615                 620

Ala Ala Glu Trp Lys Trp Ala Ser Asn Ala Lys Ser Asn Asp Glu Val
625                 630                 635                 640

Gln Val Val Leu Ala Ala Ala Gly Asp Val Pro Thr Gln Glu Ile Met
                645                 650                 655

Ala Ala Ser Asp Ala Leu Asn Lys Met Gly Ile Lys Phe Lys Val Val
            660                 665                 670

Asn Val Val Asp Leu Ile Lys Leu Gln Ser Ser Lys Glu Asn Asp Glu
        675                 680                 685

Ala Met Ser Asp Glu Asp Phe Ala Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
                725                 730                 735

Gln Gly Ser Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
        755                 760                 765

Lys Tyr Ala Asp Lys Ile Asn Glu Leu Asn Glu Phe Arg Lys Thr Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Thr Ala Gly Asp Asn Glu
            820                 825

<210> SEQ ID NO 19
<211> LENGTH: 813
<212> TYPE: PRT
<213> ORGANISM: Leuconostoc mesenteroides
<220> FEATURE:
<221> NAME/KEY: MISC_FEATURE
<222> LOCATION: (1)..(813)
<223> OTHER INFORMATION: L. mesenteroides xylulose-5P/fructose-6P
      phosphoketolase (Lmes_XFP.orf) amino acid sequence

<400> SEQUENCE: 19

```
Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Lys Ala Glu Asp Val
        35                  40                  45

Lys Val Lys Ser Ile Gly His Trp Gly Thr Ile Ser Gly Gln Thr Phe
    50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gln Val Met Val Thr Asn
                85                  90                  95

Ala Tyr Leu Asp Gly Ala Tyr Thr Glu Asp Tyr Pro Glu Ile Thr Gln
            100                 105                 110

Asp Ile Glu Gly Met Ser His Leu Phe Lys Arg Phe Ser Phe Pro Gly
            115                 120                 125

Gly Ile Gly Ser His Met Thr Ala Gln Thr Pro Gly Ser Leu His Glu
        130                 135                 140

Gly Gly Glu Leu Gly Tyr Ser Leu Ser His Ala Phe Gly Ala Val Leu
145                 150                 155                 160

Asp Asn Pro Asp Gln Val Ala Phe Ala Val Val Gly Asp Gly Glu Ala
                165                 170                 175

Glu Thr Gly Pro Ser Met Ala Ser Trp His Ser Ile Lys Phe Leu Asn
            180                 185                 190

Ala Lys Asn Asp Gly Ala Val Leu Pro Val Leu Asp Leu Asn Gly Phe
        195                 200                 205

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
                245                 250                 255

Leu Asp Gln Ala Ile Glu Asp Ile Gln Ala Ile Gln Asn Asp Ala Arg
            260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
    290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
                325                 330                 335

Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365

Asn Pro Ile Thr Asn Gly Gly Ala Asp Arg Ser Asp Leu Lys Leu Pro
    370                 375                 380

Asn Trp Arg Glu Phe Ala Asn Asp Ile Asn Asp Asn Thr Arg Gly Lys
385                 390                 395                 400
```

```
Glu Phe Ala Asp Ser Lys Arg Asn Met Asp Met Ala Thr Leu Ser Asn
                405                 410                 415

Tyr Leu Gly Ala Val Ser Gln Leu Asn Pro Thr Arg Phe Arg Phe Phe
            420                 425                 430

Gly Pro Asp Glu Thr Met Ser Asn Arg Leu Trp Gly Leu Phe Asn Val
        435                 440                 445

Thr Pro Arg Gln Trp Met Glu Glu Ile Lys Glu Pro Gln Asp Gln Leu
    450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
                485                 490                 495

Phe Ala Ser Tyr Glu Ser Phe Leu Arg Val Val Asp Thr Met Val Thr
            500                 505                 510

Gln His Phe Lys Trp Leu Arg His Ala Ser Glu Gln Ala Trp Arg Asn
        515                 520                 525

Asp Tyr Pro Ser Leu Asn Leu Ile Ala Thr Ser Thr Ala Phe Gln Gln
    530                 535                 540

Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
                565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
    610                 615                 620

Trp Ala Ser Thr Ala Pro Ser Gly Asp Val Asp Ile Thr Phe Ala Ser
625                 630                 635                 640

Ala Gly Thr Glu Pro Thr Ile Glu Thr Leu Ala Ala Leu Trp Leu Ile
                645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
    690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
                725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Glu Ile Leu Ser Ala Asn
        755                 760                 765

Gly Lys Ile Asp Gln Ala Ala Ala Asp Thr Phe Ile Ala Lys Met Asp
    770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810
```

<210> SEQ ID NO 20
<211> LENGTH: 323
<212> TYPE: PRT
<213> ORGANISM: Bacillus subtilis
<220> FEATURE:
<221> NAME/KEY: MISC_FEATURE
<222> LOCATION: (1)..(323)
<223> OTHER INFORMATION: B. subtilis phosphotransacetylase (Bs_PTA.orf) amino acid sequence

<400> SEQUENCE: 20

Met Ala Asp Leu Phe Ser Thr Val Gln Glu Lys Val Ala Gly Lys Asp
1               5                   10                  15

Val Lys Ile Val Phe Pro Glu Gly Leu Asp Glu Arg Ile Leu Glu Ala
            20                  25                  30

Val Ser Lys Leu Ala Gly Asn Lys Val Leu Asn Pro Ile Val Ile Gly
        35                  40                  45

Asn Glu Asn Glu Ile Gln Ala Lys Ala Lys Glu Leu Asn Leu Thr Leu
50                  55                  60

Gly Gly Val Lys Ile Tyr Asp Pro His Thr Tyr Glu Gly Met Glu Asp
65                  70                  75                  80

Leu Val Gln Ala Phe Val Glu Arg Arg Lys Gly Lys Ala Thr Glu Glu
                85                  90                  95

Gln Ala Arg Lys Ala Leu Leu Asp Glu Asn Tyr Phe Gly Thr Met Leu
            100                 105                 110

Val Tyr Lys Gly Leu Ala Asp Gly Leu Val Ser Gly Ala Ala His Ser
        115                 120                 125

Thr Ala Asp Thr Val Arg Pro Ala Leu Gln Ile Ile Lys Thr Lys Glu
130                 135                 140

Gly Val Lys Lys Thr Ser Gly Val Phe Ile Met Ala Arg Gly Glu Glu
145                 150                 155                 160

Gln Tyr Val Phe Ala Asp Cys Ala Ile Asn Ile Ala Pro Asp Ser Gln
                165                 170                 175

Asp Leu Ala Glu Ile Ala Ile Glu Ser Ala Asn Thr Ala Lys Met Phe
            180                 185                 190

Asp Ile Glu Pro Arg Val Ala Met Leu Ser Phe Ser Thr Lys Gly Ser
        195                 200                 205

Ala Lys Ser Asp Glu Thr Glu Lys Val Ala Asp Ala Val Lys Ile Ala
210                 215                 220

Lys Glu Lys Ala Pro Glu Leu Thr Leu Asp Gly Glu Phe Gln Phe Asp
225                 230                 235                 240

Ala Ala Phe Val Pro Ser Val Ala Glu Lys Ala Pro Asp Ser Glu
                245                 250                 255

Ile Lys Gly Asp Ala Asn Val Phe Val Phe Pro Ser Leu Glu Ala Gly
            260                 265                 270

Asn Ile Gly Tyr Lys Ile Ala Gln Arg Leu Gly Asn Phe Glu Ala Val
        275                 280                 285

Gly Pro Ile Leu Gln Gly Leu Asn Met Pro Val Asn Asp Leu Ser Arg
290                 295                 300

Gly Cys Asn Ala Glu Asp Val Tyr Asn Leu Ala Leu Ile Thr Ala Ala
305                 310                 315                 320

Gln Ala Leu

<210> SEQ ID NO 21
<211> LENGTH: 325
<212> TYPE: PRT

```
<213> ORGANISM: Lactobacillus plantarum
<220> FEATURE:
<221> NAME/KEY: MISC_FEATURE
<222> LOCATION: (1)..(325)
<223> OTHER INFORMATION: L. plantarum phosphotransacetylase
      (Lpla_PTA.orf) amino acid sequence

<400> SEQUENCE: 21
```

Met Asp Leu Phe Glu Ser Leu Ser Gln Lys Ile Thr Gly Gln Asp Gln
1               5                   10                  15

Thr Ile Val Phe Pro Glu Gly Thr Glu Pro Arg Ile Val Gly Ala Ala
            20                  25                  30

Ala Arg Leu Ala Ala Asp Gly Leu Val Lys Pro Ile Val Leu Gly Ala
        35                  40                  45

Thr Asp Lys Val Gln Ala Val Ala Lys Asp Leu Asn Ala Asp Leu Thr
50                  55                  60

Gly Val Gln Val Leu Asp Pro Ala Thr Tyr Pro Ala Glu Asp Lys Gln
65                  70                  75                  80

Ala Met Leu Asp Ser Leu Val Glu Arg Arg Lys Gly Lys Asn Thr Pro
                85                  90                  95

Glu Gln Ala Ala Lys Met Leu Glu Asp Glu Asn Tyr Phe Gly Thr Met
            100                 105                 110

Leu Val Tyr Met Gly Lys Ala Asp Gly Met Val Ser Gly Ala Val His
        115                 120                 125

Pro Thr Gly Asp Thr Val Arg Pro Ala Leu Gln Ile Ile Lys Thr Lys
130                 135                 140

Pro Gly Ser His Arg Ile Ser Gly Ala Phe Ile Met Gln Lys Gly Glu
145                 150                 155                 160

Glu Arg Tyr Val Phe Ala Asp Cys Ala Ile Asn Ile Asp Pro Asp Ala
                165                 170                 175

Asp Thr Leu Ala Glu Ile Ala Thr Gln Ser Ala Ala Thr Ala Lys Val
            180                 185                 190

Phe Asp Ile Asp Pro Lys Val Ala Met Leu Ser Phe Ser Thr Lys Gly
        195                 200                 205

Ser Ala Lys Gly Asp Met Val Thr Lys Val Gln Glu Ala Thr Ala Lys
210                 215                 220

Ala Gln Ala Ala Ala Pro Glu Leu Ala Ile Asp Gly Glu Met Gln Phe
225                 230                 235                 240

Asp Ala Ala Phe Val Glu Lys Val Gly Leu Gln Lys Ala Pro Gly Ser
                245                 250                 255

Lys Val Ala Gly His Ala Asn Val Phe Val Phe Pro Glu Leu Gln Ser
            260                 265                 270

Gly Asn Ile Gly Tyr Lys Ile Ala Gln Arg Phe Gly His Phe Glu Ala
        275                 280                 285

Val Gly Pro Val Leu Gln Gly Leu Asn Lys Pro Val Ser Asp Leu Ser
290                 295                 300

Arg Gly Cys Ser Glu Glu Asp Val Tyr Lys Val Ala Ile Ile Thr Ala
305                 310                 315                 320

Ala Gln Gly Leu Ala
                325

```
<210> SEQ ID NO 22
<211> LENGTH: 556
<212> TYPE: PRT
<213> ORGANISM: Bifidobacterium adoloscentis
<220> FEATURE:
<221> NAME/KEY: MISC_FEATURE
```

<222> LOCATION: (1)..(556)
<223> OTHER INFORMATION: B. adoloscentis phosphotransacetylase
      (Bado_PTA.orf) amino acid sequence

<400> SEQUENCE: 22

```
Met Ser Phe Thr Ser Val Thr Ile Ile Ser Pro Glu Ala Ala Asn Gly
1               5                   10                  15

Arg Asn Val Val Ala Leu Gly Val Thr Lys Thr Leu Ala Ala Ala Gly
                20                  25                  30

Lys Thr Gly Val Phe Arg Pro Ala Val Cys Arg Lys Asp Thr Phe Thr
            35                  40                  45

Asp Val Leu Ile Glu Ala Ser Asn Ala Gly Leu Ser Arg Glu Gln Ser
        50                  55                  60

Val Gly Val Cys Pro Lys Arg Ala Arg Asn Asp Lys Glu Gly Ser Arg
65                  70                  75                  80

Ala Asp Ile Val Ala Ala Tyr Thr Gln Ala Val Glu Thr Ala Arg Pro
                85                  90                  95

Asp Ala Met Val Ile Val Gly Thr Asp Arg Ser Ala Val Asn Asp Pro
            100                 105                 110

Ala Met Phe Ser Phe Asn Ala Asp Val Ala Ala Asp Leu Gln Ser Pro
        115                 120                 125

Val Leu Leu Ala Val Cys Thr Ile Glu Arg Thr Pro Glu Gln Val Lys
130                 135                 140

Ser Thr Val Glu Ala Ser Thr Lys Val Ile Glu Asp Ala Gly Ser Lys
145                 150                 155                 160

Val Val Gly Val Phe Ile Thr Gly Cys Asp Asp Thr Gln Pro Asn Pro
                165                 170                 175

Leu Lys Ala Cys Phe Val Asp Tyr Pro Val Pro Val Trp Thr Leu Pro
            180                 185                 190

Ala Val Asp Phe Asn Asp Asp Ala Ile Ser Lys Ala Asp Glu Ala
        195                 200                 205

Phe Ala Thr Asn Val Asp Ala Val Glu Leu Thr Val Ala Leu Glu Ser
        210                 215                 220

Pro Phe Asp Ala Pro Thr Thr Pro Tyr Ala Phe Gln Tyr Gly Leu Leu
225                 230                 235                 240

Gly Lys Ala Lys Ala Asp Lys Lys Thr Ile Val Leu Pro Glu Gly Asn
                245                 250                 255

Glu Asp Arg Ile Ile Lys Ala Ala Asp Tyr Leu Leu Glu Arg Asp Ile
            260                 265                 270

Val Asp Leu Ile Ile Val Gly Asp Glu Asn Ala Ile Leu Ala Arg Gly
        275                 280                 285

Gln Glu Leu Gly Leu Lys Ser Leu Gly Lys Ala Lys Phe Gln Ala Lys
    290                 295                 300

Asp Asp Glu Thr Val Leu Glu Pro Met Val Ala Lys Leu Cys Glu Leu
305                 310                 315                 320

Arg Ala Lys Lys Gly Met Thr Glu Glu Gln Ala Arg Lys Gln Leu Ala
                325                 330                 335

Asp Asp Ser Tyr Phe Gly Thr Met Leu Val Val Met Gly Met Ala Asp
            340                 345                 350

Gly Leu Val Ser Gly Ser Val Asn Ser Thr Ala Asn Thr Val Arg Pro
        355                 360                 365

Ala Leu Gln Val Ile Lys Thr Lys Pro Gly Thr Ser Leu Val Ser Gly
        370                 375                 380
```

```
Ala Phe Leu Met Cys Phe Lys Asp His Ala Ala Val Phe Asp Cys
385                 390                 395                 400

Ala Ile Asn Leu Asn Pro Asn Ala Glu Gln Leu Ala Glu Ile Ala Ile
            405                 410                 415

Gln Ser Ala Glu Thr Ala Lys Ala Phe Gly Leu Glu Pro Lys Val Gly
        420                 425                 430

Met Leu Ser Tyr Ser Thr Leu Gly Ser Gly Lys Gly Pro Asp Val Asp
            435                 440                 445

Leu Val Glu Glu Ala Thr Thr Ile Val Lys Asp Lys Ala Pro Asp Leu
450                 455                 460

Ala Val Val Gly Ser Ile Gln Phe Asp Ala Ala Trp Ser Pro Thr Val
465                 470                 475                 480

Ala Ala Thr Lys Ala Lys Gly Asp Pro Val Ala Gly His Val Asn Val
            485                 490                 495

Phe Val Phe Pro Asp Leu Cys Ala Gly Asn Ile Ala Tyr Lys Ala Val
            500                 505                 510

Gln Arg Ser Ser Gly Ala Ala Ala Val Gly Pro Val Leu Gln Gly Leu
        515                 520                 525

Asn Arg Pro Val Asn Asp Leu Ser Arg Gly Ala Thr Val Gln Asp Ile
530                 535                 540

Ile Asn Thr Ile Ala Leu Thr Ala Ile Glu Ala Gln
545                 550                 555

<210> SEQ ID NO 23
<211> LENGTH: 333
<212> TYPE: PRT
<213> ORGANISM: Methosarcina thermophila
<220> FEATURE:
<221> NAME/KEY: MISC_FEATURE
<222> LOCATION: (1)..(333)
<223> OTHER INFORMATION: M. thermophila phosphotransacetylase
      (Mthe_PTA.orf) amino acid sequence

<400> SEQUENCE: 23

Met Val Thr Phe Leu Glu Lys Ile Ser Glu Arg Ala Lys Lys Leu Asn
1               5                   10                  15

Lys Thr Ile Ala Leu Pro Glu Thr Glu Asp Ile Arg Thr Leu Gln Ala
            20                  25                  30

Ala Ala Lys Ile Leu Glu Arg Gly Ile Ala Asp Ile Val Leu Val Gly
        35                  40                  45

Asn Glu Ala Asp Ile Lys Ala Leu Ala Gly Asp Leu Asp Leu Ser Lys
    50                  55                  60

Ala Lys Ile Val Asp Pro Lys Thr Tyr Glu Lys Lys Asp Glu Tyr Ile
65                  70                  75                  80

Asn Ala Phe Tyr Glu Leu Arg Lys His Lys Gly Ile Thr Leu Glu Asn
                85                  90                  95

Ala Ala Glu Ile Met Ser Asp Tyr Val Tyr Phe Ala Val Met Met Ala
            100                 105                 110

Lys Leu Gly Glu Val Asp Gly Val Val Ser Gly Ala Ala His Ser Ser
        115                 120                 125

Ser Asp Thr Leu Arg Pro Ala Val Gln Ile Val Lys Thr Ala Lys Gly
    130                 135                 140

Ala Ala Leu Ala Ser Ala Phe Phe Ile Ile Ser Val Pro Asp Cys Glu
145                 150                 155                 160

Tyr Gly Ser Asp Gly Thr Phe Leu Phe Ala Asp Ser Gly Met Val Glu
                165                 170                 175
```

```
Met Pro Ser Val Glu Asp Val Ala Asn Ile Ala Val Ile Ser Ala Lys
            180                 185                 190

Thr Phe Glu Leu Leu Val Gln Asp Val Pro Lys Val Ala Met Leu Ser
            195                 200                 205

Tyr Ser Thr Lys Gly Ser Ala Lys Ser Lys Leu Thr Glu Ala Thr Ile
            210                 215                 220

Ala Ser Thr Lys Leu Ala Gln Glu Leu Ala Pro Asp Ile Ala Ile Asp
225                 230                 235                 240

Gly Glu Leu Gln Val Asp Ala Ala Ile Val Pro Lys Val Ala Ala Ser
                    245                 250                 255

Lys Ala Pro Gly Ser Pro Val Ala Gly Lys Ala Asn Val Phe Ile Phe
            260                 265                 270

Pro Asp Leu Asn Cys Gly Asn Ile Ala Tyr Lys Ile Ala Gln Arg Leu
            275                 280                 285

Ala Lys Ala Glu Ala Tyr Gly Pro Ile Thr Gln Gly Leu Ala Lys Pro
            290                 295                 300

Ile Asn Asp Leu Ser Arg Gly Cys Ser Asp Glu Asp Ile Val Gly Ala
305                 310                 315                 320

Val Ala Ile Thr Cys Val Gln Ala Ala Gln Asp Lys
            325                 330

<210> SEQ ID NO 24
<211> LENGTH: 409
<212> TYPE: PRT
<213> ORGANISM: Bifidobacterium adolescentis
<220> FEATURE:
<221> NAME/KEY: MISC_FEATURE
<222> LOCATION: (1)..(409)
<223> OTHER INFORMATION: B. adolescentis acetate kinase (Bado_ACK) amino
      acid sequence

<400> SEQUENCE: 24

Met Ala Lys Thr Val Leu Val Ile Asn Ser Gly Ser Ser Ile Lys
1               5                   10                  15

Tyr Gln Leu Val Asp Leu Glu Thr Gly Glu Gly Ile Ala Ser Gly Leu
            20                  25                  30

Val Glu Lys Ile Gly Glu Pro Val Asp Gly His Tyr Lys His Glu Tyr
            35                  40                  45

Asn Gly Glu Lys His Glu Leu Glu Glu Pro Ile His Asp His Glu Gln
        50                  55                  60

Gly Leu Lys Arg Val Leu Gly Phe Phe Asp Glu Phe Gly Pro Lys Leu
65                  70                  75                  80

Ala Asp Ala Gly Ile Val Ala Val Gly His Arg Val Val Gln Gly Gly
                85                  90                  95

Ser Ile Phe Pro Lys Pro Ala Leu Val Asn Asp Lys Thr Ile Gly Gln
            100                 105                 110

Val Lys Asp Leu Ala Val Leu Ala Pro Leu His Asn Gly Pro Glu Ala
            115                 120                 125

Lys Gly Ala Glu Val Met Arg Ser Leu Leu Pro Asp Val Pro Gln Ile
130                 135                 140

Phe Val Phe Asp Ser Ser Phe Phe Gln Leu Pro Lys Ala Ser Ser
145                 150                 155                 160

Thr Tyr Ala Leu Asn Lys Glu Val Ala Gln Gln Tyr His Ile Arg Arg
            165                 170                 175

Tyr Gly Ala His Gly Thr Ser His Glu Phe Ile Ser Ser Val Val Pro
            180                 185                 190
```

Ser Val Ile Gly Lys Pro Ala Glu Gly Leu Lys Gln Ile Val Leu His
        195                 200                 205

Ile Gly Asn Gly Ala Ser Ala Ser Ala Glu Ile Ser Gly Lys Pro Val
210                 215                 220

Glu Thr Ser Met Gly Leu Thr Pro Leu Glu Gly Leu Val Met Gly Gly
225                 230                 235                 240

Arg Thr Gly Asp Ile Asp Pro Ala Val Val Phe His Leu Ile Arg Asn
                245                 250                 255

Ala His Met Ser Val Asp Glu Leu Asp Thr Leu Phe Asn Lys Arg Ser
            260                 265                 270

Gly Met Met Gly Leu Thr Gly Phe Gly Asp Leu Arg Glu Val His Arg
        275                 280                 285

Leu Val Glu Glu Gly Asn Glu Asp Ala Lys Leu Ala Leu Asp Ile Tyr
    290                 295                 300

Val His Arg Ile Val Gly Tyr Ile Gly Asn Tyr Thr Ala Gln Met Gly
305                 310                 315                 320

Gly Val Asp Val Ile Thr Phe Thr Ala Gly Val Gly Glu Asn Asp Asp
                325                 330                 335

Val Val Arg Lys Met Val Cys Asp Lys Leu Ala Pro Phe Gly Val Lys
            340                 345                 350

Leu Asp Glu Glu Lys Asn Ala Thr Arg Ser Lys Glu Pro Arg Ile Ile
        355                 360                 365

Ser Thr Pro Asp Ser Ala Val Thr Ile Cys Val Ile Pro Thr Asn Glu
    370                 375                 380

Glu Leu Ala Ile Ala Arg Lys Ser Ala Ala Ile Ala Glu Glu Gly Lys
385                 390                 395                 400

Asp Ser Tyr Gly Asn Val Phe Ser Lys
                405

<210> SEQ ID NO 25
<211> LENGTH: 420
<212> TYPE: PRT
<213> ORGANISM: Aspergillus nidulans
<220> FEATURE:
<221> NAME/KEY: MISC_FEATURE
<222> LOCATION: (1)..(420)
<223> OTHER INFORMATION: A. nidulans ACK (Ani_ACK) amino acid sequence

<400> SEQUENCE: 25

Met Pro Arg Lys Ser Ile Leu Ser Val Asn Ala Gly Ser Ser Ser Val
1               5                   10                  15

Lys Ile Thr Phe Tyr Ser Tyr Thr Lys Thr Pro Ser Val Ile Ala Thr
            20                  25                  30

Ala Gln Val Ser Gly Ile Thr Ala Pro Pro Ala Thr Phe Lys Tyr Ser
        35                  40                  45

Val Gly Ser Lys Gln Lys Lys Glu Leu Lys Glu Lys Ile Ser Ser
    50                  55                  60

Gly Pro Asp Ala Phe Lys Leu Leu Leu His Arg Cys Phe Thr Asp Ser
65                  70                  75                  80

Asp Leu Lys Asp Val Ala Ser Ala Asp Leu Ala Tyr Ile Cys His
                85                  90                  95

Arg Val Val His Gly Gly Asp Phe Glu Ser Pro Val Val Ile Asn Glu
                100                 105                 110

Glu Thr Tyr His Gln Leu Glu Asp Leu Glu Asp Leu Ala Pro Leu His
        115                 120                 125

Asn Phe Ala Ala Leu Glu Ile Val Arg Leu Cys Lys Lys Glu Leu Pro
130                 135                 140

Asn Val Gln Ser Ile Thr Phe Asp Ser Ser Phe His Lys Ser Leu
145                 150                 155                 160

Pro Pro Tyr Val Lys Thr Tyr Pro Ile Asp Gln Glu Thr Ala Arg Arg
                165                 170                 175

Asn Lys Leu Arg Lys Tyr Gly Phe His Gly Ile Ser Tyr Ser Phe Ile
                180                 185                 190

Leu Arg Ser Val Ala Glu Tyr Leu Asn Lys Pro Val Glu Lys Thr Ser
                195                 200                 205

Leu Ile Ala Leu His Ile Gly Ser Gly Ala Ser Val Cys Ala Ile Lys
210                 215                 220

Asp Gly Lys Ser Ile Asp Thr Ser Met Gly Leu Thr Pro Leu Ala Gly
225                 230                 235                 240

Leu Pro Gly Ala Thr Arg Ser Gly Asp Ile Asp Pro Ser Leu Val Phe
                245                 250                 255

His Tyr Thr Asn Glu Ala Gly Lys Leu Ser Pro Ala Ser Thr Lys Glu
                260                 265                 270

Met His Ile Ser Thr Ala Glu Glu Ile Leu Asn Lys Lys Ser Gly Trp
                275                 280                 285

Lys Val Leu Thr Gly Thr Thr Asp Phe Ser Gln Ile Ala Val Glu Asp
290                 295                 300

Pro Pro Ser Glu Gln His Lys Leu Ala Phe Asp Ile Leu Val Asp Arg
305                 310                 315                 320

Ile Val Gly Tyr Ile Gly Asn Tyr Tyr Val Lys Leu Asp Gly Gln Val
                325                 330                 335

Glu Gly Ile Val Phe Ala Gly Ile Gly Glu Lys Ser Ala Leu Leu
                340                 345                 350

Arg Lys Ala Val Ile Glu Gln Thr Arg Cys Leu Gly Phe Ala Val Asp
                355                 360                 365

Pro Glu Lys Asn Gln His Gly Pro Gly Asp Glu Thr Val Val Asp
                370                 375                 380

Ile Thr Ala Ser Gly Arg Ser Asp Val Lys Arg Val Phe Ile Cys Gln
385                 390                 395                 400

Thr Asp Glu Gln Phe Glu Met Ala Tyr Asn Cys Thr Lys Thr Gln Gly
                405                 410                 415

Leu Asp Lys Gln
                420

<210> SEQ ID NO 26
<211> LENGTH: 506
<212> TYPE: PRT
<213> ORGANISM: Saccharomyces cerevisiae
<220> FEATURE:
<221> NAME/KEY: MISC_FEATURE
<222> LOCATION: (1)..(506)
<223> OTHER INFORMATION: Saccharomyces cerevisiae (ALDH2) aldehyde
      dehydrogenase amino acid sequence

<400> SEQUENCE: 26

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

```
Ile Thr Ser Phe Gln Ala Ala Asn Glu Lys Asp Val Asp Lys Ala Val
    50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
                100                 105                 110

Tyr His Ser Asn Ala Lys Gly Asp Leu Ala Gln Ile Leu Gln Leu Thr
                115                 120                 125

Arg Tyr Phe Ala Gly Ser Ala Asp Lys Phe Asp Lys Gly Ala Thr Ile
130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Trp Lys Leu Gln Gly Ala Leu Ala Ala Gly Asn Thr Val Ile Ile Lys
                180                 185                 190

Pro Ala Glu Asn Thr Ser Leu Ser Leu Leu Tyr Phe Ala Thr Leu Ile
                195                 200                 205

Lys Lys Ala Gly Phe Pro Pro Gly Val Val Asn Ile Val Pro Gly Tyr
210                 215                 220

Gly Ser Leu Val Gly Gln Ala Leu Ala Ser His Met Asp Ile Asp Lys
225                 230                 235                 240

Ile Ser Phe Thr Gly Ser Thr Lys Val Gly Gly Phe Val Leu Glu Ala
                245                 250                 255

Ser Gly Gln Ser Asn Leu Lys Asp Val Thr Leu Glu Cys Gly Gly Lys
                260                 265                 270

Ser Pro Ala Leu Val Phe Glu Asp Ala Asp Leu Asp Lys Ala Ile Asp
                275                 280                 285

Trp Ile Ala Ala Gly Ile Phe Tyr Asn Ser Gly Gln Asn Cys Thr Ala
                290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
                340                 345                 350

Gln Tyr Asp Arg Ile Lys Ser Tyr Ile Glu Arg Gly Lys Arg Glu Glu
                355                 360                 365

Lys Leu Asp Met Phe Gln Thr Ser Glu Phe Pro Ile Gly Gly Ala Lys
                370                 375                 380

Gly Tyr Phe Ile Pro Pro Thr Ile Phe Thr Asp Val Pro Gln Thr Ser
385                 390                 395                 400

Lys Leu Leu Gln Asp Glu Ile Phe Gly Pro Val Val Val Ser Lys
                405                 410                 415

Phe Thr Asn Tyr Asp Asp Ala Leu Lys Leu Ala Asn Asp Thr Cys Tyr
                420                 425                 430

Gly Leu Ala Ser Ala Val Phe Thr Lys Asp Val Lys Lys Ala His Met
                435                 440                 445

Phe Ala Arg Asp Ile Lys Ala Gly Thr Val Trp Ile Asn Ser Ser Asn
450                 455                 460
```

```
Asp Glu Asp Val Thr Val Pro Phe Gly Gly Phe Lys Met Ser Gly Ile
465                 470                 475                 480

Gly Arg Glu Leu Gly Gln Ser Gly Val Asp Thr Tyr Leu Gln Thr Lys
                485                 490                 495

Ala Val His Ile Asn Leu Ser Leu Asp Asn
                500                 505

<210> SEQ ID NO 27
<211> LENGTH: 506
<212> TYPE: PRT
<213> ORGANISM: Saccharomyces cerevisiae
<220> FEATURE:
<221> NAME/KEY: MISC_FEATURE
<222> LOCATION: (1)..(506)
<223> OTHER INFORMATION: Saccharomyces cerevisiae (ALDH3) aldehyde
      dehydrogenase amino acid sequence

<400> SEQUENCE: 27

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

Ile Thr Ser Phe Gln Ala Ala Asn Glu Lys Asp Val Asp Lys Ala Val
    50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
                100                 105                 110

Phe His Ser Asn Ala Lys Gln Asp Leu Ala Gln Ile Ile Glu Leu Thr
            115                 120                 125

Arg Tyr Tyr Ala Gly Ala Val Asp Lys Phe Asn Met Gly Glu Thr Ile
    130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Arg Lys Met Gln Gly Ala Leu Ala Ala Gly Asn Thr Val Ile Ile Lys
                180                 185                 190

Pro Ala Glu Asn Thr Ser Leu Ser Leu Leu Tyr Phe Ala Thr Leu Ile
            195                 200                 205

Lys Lys Ala Gly Phe Pro Pro Gly Val Val Asn Val Ile Pro Gly Tyr
    210                 215                 220

Gly Ser Val Val Gly Lys Ala Leu Gly Thr His Met Asp Ile Asp Lys
225                 230                 235                 240

Ile Ser Phe Thr Gly Ser Thr Lys Val Gly Gly Ser Val Leu Glu Ala
                245                 250                 255

Ser Gly Gln Ser Asn Leu Lys Asp Ile Thr Leu Glu Cys Gly Gly Lys
                260                 265                 270

Ser Pro Ala Leu Val Phe Glu Asp Ala Asp Leu Asp Lys Ala Ile Glu
            275                 280                 285

Trp Val Ala Asn Gly Ile Phe Phe Asn Ser Gly Gln Ile Cys Thr Ala
    290                 295                 300
```

-continued

```
Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Lys Glu Glu
        355                 360                 365

Lys Leu Asp Met Phe Gln Thr Ser Glu Phe Pro Ile Gly Gly Ala Lys
370                 375                 380

Gly Tyr Phe Ile Pro Pro Thr Ile Phe Thr Asp Val Pro Glu Thr Ser
385                 390                 395                 400

Lys Leu Leu Arg Asp Glu Ile Phe Gly Pro Val Val Val Ser Lys
                405                 410                 415

Phe Thr Asn Tyr Asp Asp Ala Leu Lys Leu Ala Asn Asp Thr Cys Tyr
                420                 425                 430

Gly Leu Ala Ser Ala Val Phe Thr Lys Asp Val Lys Lys Ala His Met
        435                 440                 445

Phe Ala Arg Asp Ile Lys Ala Gly Thr Val Trp Ile Asn Gln Thr Asn
450                 455                 460

Gln Glu Glu Ala Lys Val Pro Phe Gly Gly Phe Lys Met Ser Gly Ile
465                 470                 475                 480

Gly Arg Glu Ser Gly Asp Thr Gly Val Asp Asn Tyr Leu Gln Ile Lys
                485                 490                 495

Ser Val His Val Asp Leu Ser Leu Asp Lys
                500                 505

<210> SEQ ID NO 28
<211> LENGTH: 1038
<212> TYPE: PRT
<213> ORGANISM: Saccharomyces cerevisiae
<220> FEATURE:
<221> NAME/KEY: MISC_FEATURE
<222> LOCATION: (1)..(1038)
<223> OTHER INFORMATION: Saccharomyces cerevisiae (ALDH4) aldehyde
      dehydrogenase amino acid sequence

<400> SEQUENCE: 28

Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Arg Gly Asp
    130                 135                 140
```

```
Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
            165                 170                 175

Thr Lys Arg Gln Pro Leu Gly Val Cys Gly Gln Ile Ile Pro Trp Asn
        180                 185                 190

Phe Pro Leu Leu Met Trp Ala Trp Lys Ile Ala Pro Ala Leu Val Thr
    195                 200                 205

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
            245                 250                 255

Asn His Pro Lys Ile Lys Lys Val Ala Phe Thr Gly Ser Thr Ala Thr
        260                 265                 270

Gly Arg His Ile Tyr Gln Ser Ala Ala Gly Leu Lys Lys Val Thr
        275                 280                 285

Leu Glu Leu Gly Gly Lys Ser Pro Asn Ile Val Phe Ala Asp Ala Glu
    290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
            325                 330                 335

Tyr Asp Lys Phe Ile Glu Glu Phe Lys Ala Ala Ser Glu Ser Ile Lys
        340                 345                 350

Val Gly Asp Pro Phe Asp Glu Ser Thr Phe Gln Gly Ala Gln Thr Ser
        355                 360                 365

Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
            405                 410                 415

Ile Val Lys Glu Glu Ile Phe Gly Pro Val Val Thr Val Thr Lys Phe
        420                 425                 430

Lys Ser Ala Asp Glu Val Ile Asn Met Ala Asn Asp Ser Glu Tyr Gly
        435                 440                 445

Leu Ala Ala Gly Ile His Thr Ser Asn Ile Asn Thr Ala Leu Lys Val
    450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
            485                 490                 495

Arg Glu Met Ser Val Asp Ala Leu Gln Asn Tyr Leu Gln Val Lys Ala
        500                 505                 510

Val Arg Ala Lys Leu Asp Glu Met Phe Ser Arg Ser Thr Leu Cys Leu
        515                 520                 525

Lys Thr Ser Ala Ser Ser Ile Gly Arg Leu Gln Leu Arg Tyr Phe Ser
    530                 535                 540

His Leu Pro Met Thr Val Pro Ile Lys Leu Pro Asn Gly Leu Glu Tyr
545                 550                 555                 560
```

```
Glu Gln Pro Thr Gly Leu Phe Ile Asn Asn Lys Phe Val Pro Ser Lys
                565                 570                 575

Gln Asn Lys Thr Phe Glu Val Ile Asn Pro Ser Thr Glu Glu Glu Ile
            580                 585                 590

Cys His Ile Tyr Glu Gly Arg Glu Asp Val Glu Glu Ala Val Gln
        595                 600                 605

Ala Ala Asp Arg Ala Phe Ser Asn Gly Ser Trp Asn Gly Ile Asp Pro
610                 615                 620

Ile Asp Arg Gly Lys Ala Leu Tyr Arg Leu Ala Glu Leu Ile Glu Gln
625                 630                 635                 640

Asp Lys Asp Val Ile Ala Ser Ile Glu Thr Leu Asp Asn Gly Lys Ala
                645                 650                 655

Ile Ser Ser Ser Arg Gly Asp Val Asp Leu Val Ile Asn Tyr Leu Lys
                660                 665                 670

Ser Ser Ala Gly Phe Ala Asp Lys Ile Asp Gly Arg Met Ile Asp Thr
        675                 680                 685

Gly Arg Thr His Phe Ser Tyr Thr Lys Arg Gln Pro Leu Gly Val Cys
    690                 695                 700

Gly Gln Ile Ile Pro Trp Asn Phe Pro Leu Leu Met Trp Ala Trp Lys
705                 710                 715                 720

Ile Ala Pro Ala Leu Val Thr Gly Asn Thr Val Leu Lys Thr Ala
                725                 730                 735

Glu Ser Thr Pro Leu Ser Ala Leu Tyr Val Ser Lys Tyr Ile Pro Gln
        740                 745                 750

Ala Gly Ile Pro Pro Gly Val Ile Asn Ile Val Ser Gly Phe Gly Lys
        755                 760                 765

Ile Val Gly Glu Ala Ile Thr Asn His Pro Lys Ile Lys Lys Val Ala
        770                 775                 780

Phe Thr Gly Ser Thr Ala Thr Gly Arg His Ile Tyr Gln Ser Ala Ala
785                 790                 795                 800

Ala Gly Leu Lys Lys Val Thr Leu Glu Leu Gly Gly Lys Ser Pro Asn
                805                 810                 815

Ile Val Phe Ala Asp Ala Glu Leu Lys Lys Ala Val Gln Asn Ile Ile
                820                 825                 830

Leu Gly Ile Tyr Tyr Asn Ser Gly Glu Val Cys Cys Ala Gly Ser Arg
        835                 840                 845

Val Tyr Val Glu Glu Ser Ile Tyr Asp Lys Phe Ile Glu Glu Phe Lys
        850                 855                 860

Ala Ala Ser Glu Ser Ile Lys Val Gly Asp Pro Phe Asp Glu Ser Thr
865                 870                 875                 880

Phe Gln Gly Ala Gln Thr Ser Gln Met Gln Leu Asn Lys Ile Leu Lys
                885                 890                 895

Tyr Val Asp Ile Gly Lys Asn Glu Gly Ala Thr Leu Ile Thr Gly Gly
            900                 905                 910

Glu Arg Leu Gly Ser Lys Gly Tyr Phe Ile Lys Pro Thr Val Phe Gly
        915                 920                 925

Asp Val Lys Glu Asp Met Arg Ile Val Lys Glu Ile Phe Gly Pro
        930                 935                 940

Val Val Thr Val Thr Lys Phe Lys Ser Ala Asp Glu Val Ile Asn Met
945                 950                 955                 960

Ala Asn Asp Ser Glu Tyr Gly Leu Ala Ala Gly Ile His Thr Ser Asn
                965                 970                 975
```

```
Ile Asn Thr Ala Leu Lys Val Ala Asp Arg Val Asn Ala Gly Thr Val
            980                 985                 990

Trp Ile Asn Thr Tyr Asn Asp Phe His His Ala Val Pro Phe Gly Gly
            995                 1000                1005

Phe Asn Ala Ser Gly Leu Gly Arg Glu Met Ser Val Asp Ala Leu
        1010                1015                1020

Gln Asn Tyr Leu Gln Val Lys Ala Val Arg Ala Lys Leu Asp Glu
        1025                1030                1035

<210> SEQ ID NO 29
<211> LENGTH: 520
<212> TYPE: PRT
<213> ORGANISM: Saccharomyces cerevisiae
<220> FEATURE:
<221> NAME/KEY: MISC_FEATURE
<222> LOCATION: (1)..(520)
<223> OTHER INFORMATION: Saccharomyces cerevisiae (ALDH5) aldehyde
      dehydrogenase amino acid sequence

<400> SEQUENCE: 29

Met Leu Ser Arg Thr Arg Ala Ala Ala Pro Asn Ser Arg Ile Phe Thr
1               5                   10                  15

Arg Ser Leu Leu Arg Leu Tyr Ser Gln Ala Pro Leu Arg Val Pro Ile
            20                  25                  30

Thr Leu Pro Asn Gly Phe Thr Tyr Glu Gln Pro Thr Gly Leu Phe Ile
            35                  40                  45

Asn Gly Glu Phe Val Ala Ser Lys Gln Lys Thr Phe Asp Val Ile
        50                  55                  60

Asn Pro Ser Asn Glu Glu Lys Ile Thr Thr Val Tyr Lys Ala Met Glu
65                  70                  75                  80

Asp Asp Val Asp Glu Ala Val Ala Ala Lys Lys Ala Phe Glu Thr
            85                  90                  95

Lys Trp Ser Ile Val Glu Pro Glu Val Arg Ala Lys Ala Leu Phe Asn
            100                 105                 110

Leu Ala Asp Leu Val Glu Lys His Gln Glu Thr Leu Ala Ala Ile Glu
            115                 120                 125

Ser Met Asp Asn Gly Lys Ser Leu Phe Cys Ala Arg Gly Asp Val Ala
            130                 135                 140

Leu Val Ser Lys Tyr Leu Arg Ser Cys Gly Gly Trp Ala Asp Lys Ile
145                 150                 155                 160

Tyr Gly Asn Val Ile Asp Thr Gly Lys Asn His Phe Thr Tyr Ser Ile
            165                 170                 175

Lys Glu Pro Leu Gly Val Cys Gly Gln Ile Ile Pro Trp Asn Phe Pro
            180                 185                 190

Leu Leu Met Trp Ser Trp Lys Ile Gly Pro Ala Leu Ala Thr Gly Asn
            195                 200                 205

Thr Val Val Leu Lys Pro Ala Glu Thr Thr Pro Leu Ser Ala Leu Phe
            210                 215                 220

Ala Ser Gln Leu Cys Gln Glu Ala Gly Ile Pro Ala Gly Val Val Asn
225                 230                 235                 240

Ile Leu Pro Gly Ser Gly Arg Val Val Gly Glu Arg Leu Ser Ala His
            245                 250                 255

Pro Asp Val Lys Lys Ile Ala Phe Thr Gly Ser Thr Ala Thr Gly Arg
            260                 265                 270

His Ile Met Lys Val Ala Ala Asp Thr Val Lys Lys Val Thr Leu Glu
            275                 280                 285
```

```
Leu Gly Gly Lys Ser Pro Asn Ile Val Phe Ala Asp Ala Asp Leu Asp
        290                 295                 300

Lys Ala Val Lys Asn Ile Ala Phe Gly Ile Phe Tyr Asn Ser Gly Glu
305                 310                 315                 320

Val Cys Cys Ala Gly Ser Arg Ile Tyr Ile Gln Asp Thr Val Tyr Glu
                325                 330                 335

Glu Val Leu Gln Lys Leu Lys Asp Tyr Thr Glu Ser Leu Lys Val Gly
            340                 345                 350

Asp Pro Phe Asp Glu Glu Val Phe Gln Gly Ala Gln Thr Ser Asp Lys
        355                 360                 365

Gln Leu His Lys Ile Leu Asp Tyr Val Asp Val Ala Lys Ser Glu Gly
    370                 375                 380

Ala Arg Leu Val Thr Gly Gly Ala Arg His Gly Ser Lys Gly Tyr Phe
385                 390                 395                 400

Val Lys Pro Thr Val Phe Ala Asp Val Lys Glu Asp Met Arg Ile Val
                405                 410                 415

Lys Glu Glu Val Phe Gly Pro Ile Val Thr Val Ser Lys Phe Ser Thr
            420                 425                 430

Val Asp Glu Val Ile Ala Met Ala Asn Asp Ser Gln Tyr Gly Leu Ala
        435                 440                 445

Ala Gly Ile His Thr Asn Asp Ile Asn Lys Ala Val Asp Val Ser Lys
    450                 455                 460

Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
                485                 490                 495

Met Gly Glu Ala Ala Leu Ser Asn Tyr Thr Gln Thr Lys Ser Val Arg
            500                 505                 510

Ile Ala Ile Asp Lys Pro Ile Arg
        515                 520

<210> SEQ ID NO 30
<211> LENGTH: 500
<212> TYPE: PRT
<213> ORGANISM: Saccharomyces cerevisiae
<220> FEATURE:
<221> NAME/KEY: MISC_FEATURE
<222> LOCATION: (1)..(500)
<223> OTHER INFORMATION: Saccharomyces cerevisiae (ALDH6) aldehyde
      dehydrogenase amino acid sequence

<400> SEQUENCE: 30

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110
```

```
Leu Asp Asn Gly Lys Thr Leu Ala Leu Ala Arg Gly Asp Val Thr Ile
            115                 120                 125

Ala Ile Asn Cys Leu Arg Asp Ala Ala Tyr Ala Asp Lys Val Asn
        130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
        210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
                260                 265                 270

Leu Gly Gly Lys Ser Ala His Leu Val Phe Asp Asp Ala Asn Ile Lys
            275                 280                 285

Lys Thr Leu Pro Asn Leu Val Asn Gly Ile Phe Lys Asn Ala Gly Gln
            290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
                340                 345                 350

Gln Gln Phe Asp Thr Ile Met Asn Tyr Ile Asp Ile Gly Lys Lys Glu
            355                 360                 365

Gly Ala Lys Ile Leu Thr Gly Gly Glu Lys Val Gly Asp Lys Gly Tyr
370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
            435                 440                 445

Lys Met Leu Lys Ala Gly Thr Val Trp Ile Asn Thr Tyr Asn Asp Phe
            450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500
```

ACETIC ACID CONSUMING STRAIN

CROSS-REFERENCE TO RELATED APPLICATIONS

This application is the National Stage entry of International Application No. PCT/EP2018/075962, filed 25 Sep. 2018, which claims priority to European Patent Application No. 17193046.4, filed 26 Sep. 2017.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-523000_ST25.txt" created on 19 Mar. 2020, and 147,551 bytes in size) is submitted concurrently with the instant application, and the entire contents of the Sequence Listing are incorporated herein by reference.

BACKGROUND

Field

Field of the Invention

The invention relates to a process for the production of ethanol from a composition comprising glucose and acetic acid in the presence of a recombinant yeast which is capable to convert acetic acid to ethanol.

Description of Related Art

Bioethanol is produced by *Saccharomyces cerevisiae* from a range of substrates including corn starch, corn fiber, and corn stover, and also from other lignocellulosic hydrolysates of non-food feedstocks (e.g. energy crops and agricultural residues). These biomass materials may contain acetic acid, either as a constituent of the material itself or formed by bacterial contamination. This acetic acid forms a potential source of ethanol.

WO2011/149353 discloses a yeast cell comprising an exogenous gene coding for an enzyme with acetaldehyde dehydrogenase activity, which gene confers to the yeast cell the ability to convert acetic acid into ethanol.

However, the conversion of acetic acid into ethanol is often incomplete. Thus, there is a need for improved acetic acid conversion.

TABLE 1

Description of the sequence listing

| SEQ ID NO: | Description |
|---|---|
| 1 | *E. coli* bifunctional NAD⁺ dependent acetylating acetaldehyde/alcohol dehydrogenase (adhE) |
| 2 | *E. coli* ethanolamine utilizing protein (eutE) |
| 3 | *L. plantarum* acetaldehyde dehydrogenase (acdH) |
| 4 | *L. innocua* acetaldehyde dehydrogenase (acdH) |
| 5 | *S. aureus* acetaldehyde/alcohol dehydrogenase (adhE) |
| 6 | *E. coli* glycerol dehydrogenase (gldA) |
| 7 | *K. pneumoniae* glycerol dehydrogenase (gldA) |
| 8 | *E. aerogenes* glycerol dehydrogenase (gldA) |
| 9 | *Y. aldovae* glycerol dehydrogenase (gldA) |

TABLE 1-continued

Description of the sequence listing

| SEQ ID NO: | Description |
|---|---|
| 10 | *S. cerevisiae* dihydroxyacetone kinase (DAK1) |
| 11 | *K. pneumoniae* dihydroxyacetone kinase (dhaK) |
| 12 | *Y. lipolytica* dihydroxyacetone kinase (DAK1) |
| 13 | *S. pombe* dihydroxyacetone kinase (DAK1) |
| 14 | *D. rerio* aquaporin 9 (T3) |
| 15 | *Z. rouxii* ZYRO0E01210p (T5) |
| 16 | *B. animalis* xylulose-5P/fructose-6P phosphoketolase |
| 17 | *B. adolescentis* xylulose-5P/fructose-6P phosphoketolase |
| 18 | *B. lactis* xylulose-5P/fructose-6P phosphoketolase |
| 19 | *L. mesenteroides* xylulose-5P/fructose-6P phosphoketolase |
| 20 | *B. subtilis* phosphotransacetylase |
| 21 | *L. plantarum* phosphotransacetylase |
| 22 | *B. adoloscentis* phosphotransacetylase |
| 23 | *M. thermophila* phosphotransacetylase |
| 24 | *B. adolescentis* acetate kinase |
| 25 | *A. nidulans* acetate kinase |
| 26 | *S. cerevisiae* aldehyde dehydrogenase ALD2 |
| 27 | *S. cerevisiae* aldehyde dehydrogenase ALD3 |
| 28 | *S. cerevisiae* aldehyde dehydrogenase ALD4 |
| 29 | *S. cerevisiae* aldehyde dehydrogenase ALD5 |
| 30 | *S. cerevisiae* aldehyde dehydrogenase ALD6 |

SUMMARY OF THE INVENTION

The invention describes a process for the production of ethanol from a composition comprising glucose and between 50 µM and 100 mM acetic acid, said process comprising fermenting said composition in the presence of a recombinant yeast which is capable to convert acetic acid anaerobically; maintaining the amount of undissociated acetic acid at a value of at least 50 µM; and recovering the ethanol. Said process is useful for both starch and cellulosic based, acetic acid containing hydrolysates and advantageously results in a greater consumption of acetic acid and thus higher ethanol yields. The step of maintaining the amount of dissociated acetic acid to a value of at least 50 µM may comprise: monitoring the amount of undissociated acetic acid in the composition, and if the amount of undissociated acetic acid drops below 50 µM; adding acid to the composition until the amount of undissociated acetic acid reaches a value of at least 50 µM, preferably by adding an acid. Alternatively, the step of maintaining the amount of undissociated acetic acid to a value of at least 50 µM may comprise monitoring the amount of undissociated acetic acid in the composition, and if the amount of undissociated acetic acid approaches 50 µM, but before the amount drops below 50 µM: adding acid to the composition until the amount of undissociated acetic acid reaches a value of above 50 µM, preferably by adding an acid. The recombinant yeast may comprise a nucleic acid sequence encoding an enzyme having acetylating acetaldehyde dehydrogenase activity (EC 1.2.1.10 or EC 1.1.1.2); a nucleic acid sequence encoding an an enzyme having acetyl-CoA synthetase activity (E.C.6.2. 1.1), and optionally a nucleic acid sequence encoding an enzyme having NAD-dependent alcohol dehydrogenase activity (EC 1.1.1.1). The recombinant yeast may further comprise a nucleic acid sequence encoding an enzyme having glycerol dehydrogenase activity. The recombinant yeast may comprise a deletion or disruption of one or more endogenous nucleotide sequences encoding an aldehyde dehydrogenase or it may have reduced aldehyde dehydrogenase activity compared to its corresponding wild-type yeast. Such cell may further comprise one or more genes coding for an enzyme having phosphoketolase (PKL) activity (EC 4.1.2.9 or EC 4.1.2.22), one or more genes coding for an enzyme having phosphotransacetylase (PTA) activity (EC 2.3.1.8), and/or one or more genes coding for an enzyme having acetate kinase (ACK) activity (EC 2.7.2.12). The recombinant yeast may also comprise a nucleic acid coding for an enzyme having dihydroxyacetone kinase activity. The recombinant yeast may further comprise a deletion or disruption of one or more endogenous nucleotide sequences encoding a glycerol-3-phosphate dehydrogenase. The recombinant yeast may also comprise a deletion or disruption of one or more endogenous nucleotide sequences encoding a glycerol 3-phosphate phosphohydrolase, such as *S. cerevisiae* GPP1 or GPP2. The recombinant yeast may also comprise a glycerol transporter. The composition may be a lignocellulosic biomass hydrolysate or a starch hydrolysate, such as a corn starch hydrolysate. The yeast may be a *Saccharomyces cerevisiae*.

DETAILED DESCRIPTION OF THE INVENTION

Expression of an exogenous acetylating acetaldehyde dehydrogenase in yeast allows the yeast to convert acetic acid, which may be present in both lignocellulosic hydrolysates and in corn starch hydrolysates, to ethanol. The NADH dependent reduction of acetic acid to ethanol has been proposed as a replacement for glycerol formation as a redox sink in anaerobic glucose-grown cultures of *S. cerevisiae*, thus providing a stoichiometric basis for elimination of glycerol production (as by-product) during industrial ethanol production and consequently a higher ethanol yield. However, the inventor has surprisingly found that when such yeast is used, there is often a residual amount of acetic acid in the fermentation media which remains unconverted. This residual amount of acetic acid may be as large as several millimolar. The inventor surprisingly found that by adding a slight amount of acid, the yeast resumed consumption of acetic acid. Realizing that adding acid forces the acetic acid to its protonated (i.e. undissociated) form, he deduced that there may be a minimal concentration of undissociated acetic acid required for the yeast to consume acetic acid. He indeed found that yeast requires a minimum concentration of undissociated acetic acid of at least 50 µM—if the amount decreases below 50 µM, the consumption of acetic acid gradually decreases and eventually stops altogether, even if there is a considerable amount of dissociated acetate present in the fermentation media. If this is the case, raising the amount of undissociated acetic acid to at a value of at least 50 µM, the acetic acid consumption proceeds to near completion. The inventor realised that the yeast only consumes undissociated acetic acid and not the dissociated form of acetic acid, and further that the yeast can consume such undissociated acetic acid only to a concentration of about 50 µM. Apparently, when the amount of undissociated acetic acid drops to a concentration of below 50 µM, the yeast stops consuming the acetic acid altogether, even if there is a considerable reservoir of acetate in the fermentation media.

Thus, the invention relates to a process for the production of ethanol from a composition comprising a sugar and between 50 µM and 100 mM acetic acid, said process comprising:
 fermenting said composition in the presence of a recombinant yeast which is capable to convert acetic acid anaerobically;
 maintaining the amount of dissociated acetic acid at a value of at least 50 µM; and recovering the ethanol.

The amount of undissociated acetic acid may be maintained at a value of at least 60 µM, at least 70, at least 80, at least 90, at least 100 µM, or at least 120 µM, at least 150 µM, or at least 200 µM.

The upper amount of undissociated acetic acid is less crucial, but may be 100 mM or less, preferably 80 mM or less, 60 mM or less, 40 mM or less, 30 mM or less, 20 mM or less 10 mM or less, 5 mM or less, 2 mM or less, 1 mM or less. If the amount of undissociated acetic acid is too high, for example 100 mM the result may be decreased growth, incomplete fermentation and/or decreased ethanol yield, possibly due to acetic acid toxicity. Since it is anticipated that the pH during the fermentation process in which acetic acid is converted to ethanol increases, the amount of undissociated acetic acid will also decrease. Thus, as long as the starting concentration acetic acid in the composition is not higher than 100 mM, the amount of undissociated acetic acid will not increase above 100 mM, and no active steps need to be taken in order to prevent the increase of undissociated acetic acid to a level above 100 mM. Hypothetically, almost all acetic acid in the composition is in the undissociated form, but this would require a very low pH value, which is not conducive for the yeast. Therefore, in an embodiment the amount of undissociated acetic acid is maintained at a value of 100 mM or less, preferably 80 mM or less, 60 mM or less, 40 mM or less, 30 mM or less, 20 mM or less 10 mM or less, 5 mM or less, 2 mM or less, 1 mM or less, for example by adding a base, such as NaOH or KOH.

In the process of the invention it is anticipated that the pH increases during fermentation as a result of consumption of acetic acid. Thus, in an embodiment the process of the invention results in an increase of pH of the composition.

In an embodiment at least part of the acetic acid is converted into ethanol.

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an amino acid" may mean one amino acid or more than one amino acid.

In the context of the invention, "maintaining the amount of dissociated acetic acid at a value of at least 50 µM" does not mean that the amount of undissociated acetic acid must never drop below 50 µM. Indeed, during the fermentation process it may so happen that the amount of undissociated acetic acid occasionally drops below 50 µM. When this occurs, the process requires restoring the amount of undissociated acetic acid to a value of at least 50 µM. In this scenario, steps to realize at least 50 µM amount of undissociated acetic acid are taken after the concentration has dropped below 50 µM. The time between the moment when the amount of dissociated acetic acid has dropped below the value of 50 µM and restoring the amount of dissociated acetic acid to a value of at least 50 µM is not crucial. This may be done instantaneously, or after 1 minute, of after 5 minutes, even after 30 minutes, or 1 hour.

Alternatively, "maintaining" may be also carried out such that the amount of undissociated acetic acid does not drop below 50 µM.

In both scenarios is it advantageous to monitor the amount of amount of undissociated acetic acid during the fermentation process.

In the context of the invention the term "undissociated acetic acid" is understood to be same as "protonated acetic acid".

The skilled person knows how to maintain the amount of undissociated acetic acid between 50 μM and 100 mM. He/she can monitor the amount of undissociated acetic acid. Thus, in an embodiment, the process comprises the step of monitoring the amount of undissociated acetic acid.

The skilled person appreciates that the amount of undissociated acetic acid depends inter alia on the total amount of acetic acid in the composition (protonated and dissociated) as well on the pH. Thus, in an embodiment the amount of dissociated acetic acid is maintained at a value of at least 50 μM by adjusting the pH. As consumption of acetic acid generally results in an increase of the pH, and as the amount of undissociated acetic acid depends inter alia on the pH such that at higher pH the amount of undissociated acetic acid decreases, when the amount of undissociated acetic acid drops below 50 mM, the pH of the composition may be decreased. This may be done by adding an acid. Therefore, in an embodiment the process comprises adding an acid. Any type of acid may suffice, for example organic acids such as citric acid, or inorganic acids such as hydrochloric acid, sulphuric acid, or nitric acid. Preferred are strong acids as weak acids may inhibit the yeast. Phosphoric acid is very suitable and may have the additional effect that the fermentation media is supplemented with phosphate. Acid may be added once, or (depending on the amount of acetic acid) two, times, three times etc during the fermentation.

Acid may be added until the amount of undissociated acetic acid reaches a value of 50 μM or higher, such as for example a value between 50 and 60 μM, or a value between 50 and 70 μM, or between 50 and 100 μM, or between 50 and 150 μM, or between 50 and 200 μM.

The process may also comprise the step of monitoring the pH. The pH of the composition is preferably kept between 3 and 6, preferably between 4 and 5. The upper limit of the pH is preferably such that the amount of undissociated acetic acid is at least 50 μM, and this depends on the total amount of acetic acid in the composition. The skilled person can readily monitor both the pH and the amount of undissociated acetic acid (see below), and adjust the pH such that the amount of undissociated acetic acid is maintained (or restored) to a value of at least 50 μM. The amount of undissociated acetic acid may be analysed by HPLC. HPLC generally measures all acetic acid and acetate salts (i.e. both undissociated, i.e. protonated form and dissociated form of acetic acid) because the mobile phase is typically acidified. In order to measure the amount of dissociated acetic acid in the composition, a suitable approach is to measure the (total) amount of acetate of the composition as-is, measure the pH of the composition, and calculate the amount of dissociated acetic acid using the pKa of acetic acid.

Thus, in an embodiment the process comprises:
monitoring the amount of undissociated acetic acid in the composition, and if the amount of undissociated acetic acid drops below 50 μM
adding acid to the composition until the amount of undissociated acetic acid reaches a value of at least 50 μM, preferably by adding an acid.

In another embodiment the process comprises:
monitoring the amount of undissociated acetic acid in the composition, and if the amount of undissociated acetic acid approaches 50 μM, but before the amount drops below 50 μM:
adding acid to the composition until the amount of undissociated acetic acid reaches a value of above 50 μM, preferably by adding an acid.

Just to avoid any doubt, the invention also includes a process for the production of ethanol from a composition comprising a sugar and between 50 μM and 100 mM acetic acid, said process comprising:
fermenting said composition in the presence of a recombinant yeast which is capable to convert acetic acid anaerobically;
monitoring the amount of undissociated acetic acid in the composition, and if the amount of undissociated acetic acid approaches 50 μM, but before the amount drops below 50 μM:
adding acid to the composition until the amount of undissociated acetic acid reaches a value of above 50 μM (such as 55 μM or more, 60 μM or more, 70 μM or more, 80 μM or more, 90 μM or more, 100 μM or more), preferably by adding an acid; and
recovering the ethanol product.

The enzyme acetylating acetaldehyde dehydrogenase (EC1.2.1.10 or EC1.1.1.2) catalyses the conversion of acetyl-Coenzyme A to acetaldehyde. This conversion can be represented by the equilibrium reaction formula (I):

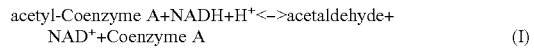

$$\text{acetyl-Coenzyme A} + \text{NADH} + \text{H}^+ \leftrightarrow \text{acetaldehyde} + \text{NAD}^+ + \text{Coenzyme A} \quad (I)$$

It is understood that the recombinant yeast used in the process of the invention naturally comprises at least one endogenous gene encoding an acetyl CoA synthetase and at least one endogenous gene encoding an alcohol dehydrogenase. Thus, in the context of this invention this recombinant yeast, which is transformed with a gene encoding an acetylating acetaldehyde dehydrogenase, and having the endogenous genes encoding acetyl CoA synthetase and alcohol dehydrogenase is capable to complete the conversion of acetic acid into ethanol.

In an embodiment the recombinant yeast comprises:
a nucleic acid sequence encoding an enzyme having acetylating acetaldehyde dehydrogenase activity (EC 1.2.1.10 or EC 1.1.1.2);
a nucleic acid sequence encoding an enzyme having acetyl-CoA synthetase activity (E.C.6.2. 1.1), and optionally
a nucleic acid sequence encoding an enzyme having NAD-dependent alcohol dehydrogenase activity (EC 1.1.1.1).

The recombinant yeast used in the process is capable to convert acetic acid anaerobically. In an embodiment, the recombinant yeast is capable to convert acetic acid to at least ethanol. In another embodiment the recombinant yeast is capable to convert each of glucose and acetic acid to at least ethanol. In the context of this invention, the terms "capable to convert acetic acid" and "capable to convert each of glucose and acetic acid" are understood to mean that at least part of the acetic acid and/or glucose is converted to at least ethanol.

The nucleic acid encoding an enzyme having acetylating acetaldehyde dehydrogenase activity is preferably NAD$^+$ dependent and may have an amino acid sequence according to SEQ ID NO: 1, 2, 3, 4, or 5 or a functional homologue thereof having a sequence identity of at least 50%, preferably at least 60%, 70%, 75%, 80%. 85%, 90% or 95% or which functional homologue is derived, by way of one or more amino acid substitutions, deletions or insertions, from the amino acid sequence of SEQ ID NO: 1, 2, 3, 4, or 5. The acetylating acetaldehyde may comprise both NAD$^+$ dependent acetylating acetaldehyde dehydrogenase (EC 1.2.1.10 or EC 1.1.1.2) activity and NAD+ dependent alcohol dehydrogenase activity (EC 1.1.1.1). The nucleic acid sequence encoding the NAD+ dependent acetylating acetaldehyde dehydrogenase may in principle originate from any organism comprising a nucleic acid sequence encoding said dehydrogenase. Known acetylating acetaldehyde dehydrogenases that can catalyse the NADH-dependent reduction of acetyl-Coenzyme A to acetaldehyde may in general be divided in three types of NAD+ dependent acetylating acetaldehyde dehydrogenase functional homologues:

1) Bifunctional proteins that catalyse the reversible conversion of acetyl-CoA to acetaldehyde, and the subsequent reversible conversion of acetaldehyde to ethanol. An example of this type of proteins is the AdhE protein in *E. coli* (Gen Bank No: NP_415757). AdhE appears to be the evolutionary product of a gene fusion. The $NH_2$— terminal region of the AdhE protein is highly homologous to aldehyde:NAD+ oxidoreductases, whereas the COOH-terminal region is homologous to a family of $Fe^{2+}$ dependent ethanol: NAD+ oxidoreductases (Memorial-Hernandez et al., (2000) J. Biol. Chern. 275: 33869-33875). The *E. coli* AdhE is subject to metal-catalyzed oxidation and therefore oxygen-sensitive (Tamarit et al. (1998) J. Biol. Chern. 273:3027-32).

2) Proteins that catalyse the reversible conversion of acetyl-Coenzyme A to acetaldehyde in strictly or facultative anaerobic micro-organisms but do not possess alcohol dehydrogenase activity. An example of this type of proteins has been reported in *Clostridium kluyveri* (Smith et al. (1980) Arch. Biochem. Biophys. 203: 663-675). An acetylating acetaldehyde dehydrogenase has been annotated in the genome of *Clostridium kluyveri* DSM 555 (GenBank No: EDK33116). A homologous protein AcdH is identified in the genome of *Lactobacillus plantarum* (GenBank No: NP_784141). Another example of this type of proteins is the said gene product in *Clostridium beijerinckii* NRRL B593 (Toth et al. (1999) Appl. Environ. Microbiol. 65: 4973-4980, GenBank No: AAD31841).

3) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) Biodegradation 5, 219-236). 4-Hydroxy-2-ketovalerate is first converted by 4-hydroxy-2-ketovalerate aldolase to pyruvate and acetaldehyde, subsequently acetaldehyde is converted by acetylating acetaldehyde dehydrogenase to acetyl-CoA. An example of this type of acetylating acetaldehyde dehydrogenase is the DmpF protein in *Pseudomonas* sp CF600 (GenBank No: CAA43226) (Shingler et al. (1992) J. Bacteriol. 174:711-24). The *E. coli* MphF protein (Ferrandez et al. (1997) J. Bacteriol. 179: 2573-2581, GenBank No: NP_414885) is homologous to the DmpF protein in *Pseudomonas* sp. CF600.

A suitable nucleic acid sequence may in particular be found in an organism selected from the group of *Escherichia*, in particular *E. coli*; *Mycobacterium*, in particular *Mycobacterium marinum*, *Mycobacterium ulcerans*, *Mycobacterium tuberculosis*; *Carboxydothermus*, in particular *Carboxydothermus hydrogenoformans*; *Entamoeba*, in particular *Entamoeba histolytica*; *Shigella*, in particular *Shigella sonnei*; *Burkholderia*, in particular *Burkholderia pseudo mallei*, *Klebsiella*, in particular *Klebsiella pneumoniae*; *Azotobacter*, in particular *Azotobacter vinelandii*; *Azoarcus* sp; *Cupriavidus*, in particular *Cupriavidus taiwanensis*; *Pseudomonas*, in particular *Pseudomonas* sp. CF600; *Pelomaculum*, in particular *Pelotomaculum thermopropionicum*. Preferably, the nucleic acid sequence encoding the NAD+ dependent acetylating acetaldehyde dehydrogenase originates from *Escherichia*, more preferably from *E. coli*.

Particularly suitable is an mhpF gene from *E. coli*, or a functional homologue thereof. This gene is described in Fernindez et al. (1997) J. Bacteriol. 179:2573-2581. Good results have been obtained with *S. cerevisiae*, wherein an mhpF gene from *E. coli* has been incorporated. In a further advantageous embodiment the nucleic acid sequence encoding an (acetylating) acetaldehyde dehydrogenase is from *Pseudomonas*, in particular dmpF, e.g. from *Pseudomonas* sp. CF600.

The nucleic acid sequence encoding the acetylating acetaldehyde dehydrogenase may be a wild type nucleic acid sequence. Further, an acetylating acetaldehyde dehydrogenase (or nucleic acid sequence encoding such activity) may in for instance be selected from the group of *Escherichia coli* adhE, *Entamoeba histolytica* adh2, *Staphylococcus aureus* adhE, *Piromyces* sp.E2 adhE, *Clostridium kluyveri* EDK33116, *Lactobacillus plantarum* acdH, *Escherichia coli* eutE, *Listeria innocua* acdH, and *Pseudomonas putida* YP 001268189. For sequences of some of these enzymes, nucleic acid sequences encoding these enzymes and methodology to incorporate the nucleic acid sequence into a host cell, reference is made to WO2009/013159, in particular Example 3, Table 1 (page 26) and the Sequence ID numbers mentioned therein, of which publication Table 1 and the sequences represented by the Sequence ID numbers mentioned in said Table are incorporated herein by reference.

Acetyl-CoA synthetase (also known as acetate-CoA ligase and acetyl-activating enzyme) is a ubiquitous enzyme, found in both prokaryotes and eukaryotes, which catalyses the formation of acetyl-CoA from acetate, coenzyme A (CoA) and ATP as shown below:

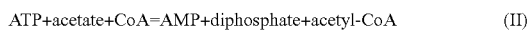

ATP+acetate+CoA=AMP+diphosphate+acetyl-CoA (II)

The activity of this enzyme is crucial for maintaining the required levels of acetyl-CoA, a key intermediate in many important biosynthetic and catabolic processes. It is especially important in eukaryotic species as it is the only route for the activation of acetate to acetyl-CoA in these organisms (some prokaryotic species can also activate acetate by either acetate kinase/phosphotransacetylase or by ADP-forming acetyl-CoA synthase). Eukaryotes typically have two isoforms of acetyl-CoA synthase, a cytosolic form involved in biosynthetic processes and a mitochondrial form primarily involved in energy generation.

The crystal structures of a eukaryotic (e.g. from yeast) and bacterial (e.g. from *Salmonella*) form of this enzyme have been determined. The yeast enzyme is trimeric, while the bacterial enzyme is monomeric. The trimeric state of the yeast protein may be unique to this organism however, as the residues involved in the trimer interface are poorly conserved in other sequences. Despite differences in the oligomeric state of the two enzyme, the structures of the monomers are almost identical. A large N-terminal domain (~500 residues) containing two parallel beta sheets is followed by a small (~110 residues) C-terminal domain containing a three-stranded beta sheet with helices. The active site occurs at the domain interface, with its contents determining the orientation of the C-terminal domain.

The recombinant yeast may comprise an overexpressed endogenous ACS. The recombinant cell may comprise a heterologous. Examples of suitable heterologous ACS are listed in table 2.

TABLE 2

BLAST Query-ACS2 from *Saccharomyces cerevisiae*

| Description | Identity (%) | Accession number |
|---|---|---|
| acetate--CoA ligase ACS2 [*Saccharomyces cerevisiae* S288c] | 100 | NP_013254.1 |
| acetyl CoA synthetase [*Saccharomyces cerevisiae* YJM789] | 99 | EDN59693.1 |
| acetate--CoA ligase [*Kluyveromyces lactis* NRRL Y-1140] | 85 | XP_453827.1 |
| acetate--CoA ligase [*Candida glabrata* CBS 138] | 83 | XP_445089.1 |
| acetate--CoA ligase [*Scheffersomyces stipitis* CBS 6054] | 68 | XP_001385819.1 |
| acetyl-coenzyme A synthetase FacA [*Aspergillus fumigatus* A1163] | 63 | EDP50475.1 |
| acetate--CoA ligase facA-*Penicillium chrysogenum* [*Penicillium chrysogenum* Wisconsin 54-1255] | 62 | XP_002564696.1 |

In an embodiment, the recombinant yeast may comprise a nucleotides coding for an enzyme having NAD$^+$ linked glycerol dehydrogenase. As used herein, a glycerol dehydrogenase catalyzes at least the following reaction:

$$\text{glycerol} + \text{NAD}^+ \Longleftrightarrow \text{glycerone} + \text{NADH} + \text{H}^+ \quad (III)$$

Thus, the two substrates of this enzyme are glycerol and NAD$^+$, whereas its three products are glycerone, NADH, and H$^+$. Glycerone and dihydroxyacetone are herein synonyms.

This enzyme belongs to the family of oxidoreductases, specifically those acting on the CH—OH group of donor with NAD$^+$ or NADP$^+$ as acceptor. The systematic name of this enzyme class is glycerol:NAD+ 2-oxidoreductase. Other names in common use include glycerin dehydrogenase, and NAD+-linked glycerol dehydrogenase. This enzyme participates in glycerolipid metabolism. Structural studies have shown that the enzyme is zinc-dependent with the active site lying between the two domains of the protein.

In an embodiment the enzyme having glycerol dehydrogenase activity is preferably a NAD$^+$ linked glycerol dehydrogenase (EC 1.1.1.6). Such enzyme may be from bacterial origin or for instance from fungal origin. An example is gldA from *E. coli*.

Alternatively, the enzyme having glycerol dehydrogenase activity is a NADP$^+$ linked glycerol dehydrogenase (EC 1.1.1.72).

When the recombinant yeast is used for ethanol production, which typically takes place under anaerobic conditions, NAD$^+$ linked glycerol dehydrogenases are preferred.

In an embodiment the recombinant yeast comprises one or more genes encoding a heterologous glycerol dehydrogenase represented by amino acid sequence SEQ ID NO: 6, 7, 8, or 9, or a functional homologue thereof a having sequence identity of at least 50%, preferably at least 60%, 70%, 75%, 80%. 85%, 90% or 95% or which functional homologue is derived, by way of one or more amino acid substitutions, deletions or insertions, from the amino acid sequence of SEQ ID NO: 6, 7, 8, or 9.

The recombinant yeast comprises a nucleic acid coding for an enzyme having dihydroxyacetone kinase activity. The dihydroxyacetone kinase enzyme catalyzes at least one of the following reactions:

$$\text{EC 2.7.1.28: ATP} + \text{D-glyceraldehyde} \Longleftrightarrow \text{ADP} + \text{D-glyceraldehyde 3-phosphate} \quad (IV)$$

or $$\text{EC 2.7.1.29: ATP} + \text{glycerone} \Longleftrightarrow \text{ADP} + \text{glycerone phosphate} \quad (V)$$

This family consists of examples of the single chain form of dihydroxyacetone kinase (also called glycerone kinase) that uses ATP (EC 2.7.1.29 or EC 2.7.1.28) as the phosphate donor, rather than a phosphoprotein as in *Escherichia coli*. This form has separable domains homologous to the K and L subunits of the *E. coli* enzyme, and is found in yeasts and other eukaryotes and in some bacteria, including *Citrobacter freundii*. The member from tomato has been shown to phosphorylate dihydroxyacetone, 3,4-dihydroxy-2-butanone, and some other aldoses and ketoses. Members from mammals have been shown to catalyse both the phosphorylation of dihydroxyacetone and the splitting of ribonucleoside diphosphate-X compounds among which FAD is the best substrate. In yeast there are two isozymes of dihydroxyacetone kinase (Dak1 and Dak2). In an embodiment the recombinant yeast comprises endogenous DAK which is overexpressed.

The enzyme having dihydroxy acetone kinase activity may be encoded by an endogenous gene, e.g. a DAK1, which endogenous gene is preferably placed under control of a constitutive promoter. The recombinant cell may comprise a genetic modification that increases the specific activity of dihydroxyacetone kinase in the cell.

In an embodiment the recombinant yeast comprises one or more nucleic acid sequences encoding a dihydroxy acetone kinase represented by amino acid sequence according to SEQ ID NO: 10, 11, 12, or 13 or by a functional homologue thereof having a sequence identity of at least 50%, preferably at least 60%, 70%, 75%, 80%. 85%, 90% or 95% or which functional homologue is derived, by way of one or more amino acid substitutions, deletions or insertions, from the amino acid sequence of SEQ ID NO: 10, 11, 12, or 13, which gene is preferably placed under control of a constitutive promoter.

In an embodiment the recombinant yeast comprises a deletion or disruption of one or more endogenous nucleotide sequences encoding a glycerol-3-phosphate dehydrogenase. Such a deletion or disruption may result in decrease or removal of enzymatic activity. As used herein, a glycerol 3-phosphate dehydrogenase catalyzes at least the following reaction:

$$\text{dihydroxyacetone phosphate} + \text{NADH} \rightarrow \text{glycerol phosphate} + \text{NAD}^+ \quad (VI)$$

Glycerol-3-phosphate dehydrogenase may be entirely deleted, or at least a part is deleted which encodes a part of the enzyme that is essential for its activity. In particular, good results have been achieved with a *S. cerevisiae* cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in *Saccharomyces cerevisiae* by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization. The deleted or disrupted glycerol-3-phosphate dehydrogenase preferably belongs to EC 1.1.5.3, such as GUT2, or to EC 1.1.1.8, such as GPD1 and or GPD2. In embodiment the cell is free of genes encoding NADH-dependent glycerol-3-phosphate dehydrogenase. Both GPD1 and GPD2 genes may be deleted or disrupted, although it is preferred that GPD2, but not GPD1 is deleted or disrupted. WO2011/010923 describes methods to delete or disrupt a glycerol-3-phosphate dehydrogenase.

In an embodiment the recombinant yeast comprises a deletion or disruption of one or more endogenous nucleotide sequences encoding a glycerol 3-phosphate phosphohydrolase, such as S. cerevisiae GPP1 or GPP2. Such a deletion or disruption may result in decrease or removal of enzymatic activity.

In an embodiment the recombinant cell comprises one or more genes coding for a glycerol transporter. Glycerol that is externally available in the medium (e.g. from the backset in corn mash) or secreted after internal cellular synthesis may be transported into the cell and converted to ethanol by the concomitant (over) expression of a glycerol dehydrogenase and dihydroxy acetone kinase. In an embodiment the recombinant cell comprises one or more genes encoding a heterologous glycerol transporter represented by SEQ ID NO: 14 or 15, or a functional homologue thereof having a sequence identity of at least 60%, preferably at least 70%, 75%, 80%. 85%, 90% or 95% or which functional homologue is derived, by way of one or more amino acid substitutions, deletions or insertions, from the amino acid sequence of SEQ ID NO: 14 or 15.

In an embodiment the composition is a biomass hydrolysate. Such biomass hydrolysate may be a lignocellulosic biomass hydrolysate. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

In another embodiment the composition is a starch hydrolysate, such as a corn starch hydrolysate.

In the context of the invention a "hydrolysate" means a polysaccharide that has been depolymerized through the addition of water to form mono and oligosaccharide sugars. Hydrolysates may be produced by enzymatic or acid hydrolysis of the polysaccharide-containing material.

"Expression" refers to the transcription of a gene into structural RNA (rRNA, tRNA) or messenger RNA (mRNA) with subsequent translation into a protein.

As used herein "promoter" is a DNA sequence that directs the transcription of a (structural) gene, in particular one or more phosphoribulokinase gene. The promoter enables higher expression during anaerobic conditions than under aerobic conditions.

The term "a" or "an" as used herein is defined as "at least one" unless specified otherwise. When referring to a noun (e.g. a compound, an additive, etc.) in the singular, the plural is meant to be included. Thus, when referring to a specific moiety, e.g. "nucleotide", this means "at least one" of that moiety, e.g. "at least one nucleotide", unless specified otherwise. The term 'or' as used herein is to be understood as 'and/or'.

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the yeast cell, in particular a yeast cell, and usually corresponds to an oxygen consumption of less than 5 mmol/l·h, in particular to an oxygen consumption of less than 2.5 mmol/l·h, or less than 1 mmol/l·h. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant" as used herein, refers to a cell containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov, (as available on 14 Jun. 2016) unless specified otherwise.

The term "functional homologue" (or in short "homologue") of a polypeptide having a specific sequence (e.g. SEQ ID NO: X), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant yeast cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity in the yeast cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows:

Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. In an embodiment, conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. In an embodiment, conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Ttyr; Ser to Thr; Thr to Ser; Trp to Tyr; Tyr to Trp or Phe; and Val to Ile or Leu.

Nucleotide sequences may be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The recombinant yeast is preferably selected from the group of Saccharomycetaceae, such as *Saccharomyces cerevisiae, Saccharomyces pastorianus, Saccharomyces beticus, Saccharomyces fermentati, Saccharomyces paradoxus, Saccharomyces uvarum* and *Saccharomyces bayanus;* Schizosaccharomyces such as *Schizosaccharomyces pombe, Schizosaccharomyces japonicus, Schizosaccharomyces octosporus* and *Schizosaccharomyces cryophilus;* Toruloaspora such as *Torulaspora delbrueckii;* Kluyveromyces such as *Kluyveromyces marxianus;* Pichia such as *Pichia stipitis, Pichia pastoris* or *pichia angusta,* Zygosaccharomyces such as *Zygosaccharomyces bailii;* Brettanomyces such as *Brettanomyces intermedius, Brettanomyces bruxellensis, Brettanomyces anomalus, Brettanomyces custersianus, Brettanomyces naardenensis, Brettanomyces nanus, Dekkera Bruxellis* and *Dekkera anomala; Metschnikowia, Issatchenkia,* such as *Issatchenkia orientalis, Kloeckera* such as *Kloeckera apiculata; Aureobasisium* such as *Aureobasidium pullulans.* A preferred yeast is *Saccharomyces cerevisiae.*

The recombinant yeast used in the process may comprise:
- a set consisting of PPP-genes TAL1, TKL1, RPE1 and RKI1, optionally under control of strong constitutive promoter;
- a set consisting of a xylA-gene under control of strong constitutive promoter;
- a set comprising a XKS1-gene under control of strong constitutive promoter, a set consisting of the genes araA, araB and araD under control of a strong constitutive promoter deletion of an aldose reductase gene.

In an embodiment the recombinant yeast comprises a deletion or disruption of one or more endogenous nucleotide sequences encoding an aldehyde dehydrogenase (E.C. 1.2.1.4) or which yeast has reduced aldehyde dehydrogenase activity compared to its corresponding wild-type yeast.

As used herein, An aldehyde dehydrogenase catalyzes at least the following reaction:

acetaldehyde+NADP$^+$+H$_2$O→acetic acid+NADPH+ H$^+$ (VII)

Said one or more nucleotide sequences encoding an aldehyde dehydrogenase preferably encodes aldehyde dehydrogenase ALD2, ALD3, ALD4, ALD5, or ALD6 or an enzyme having an amino acid sequence according SEQ ID NO: 16, 27, 28, 29 or 30, or a functional homologues thereof having a sequence identity of at least 50%, preferably at least 60%, more preferably at least 70%, 75%, 80%, 85%, 90% or 95%, or which functional homologue is derived, by way of one or more amino acid substitutions, deletions or insertions, from the amino acid sequence of SEQ ID NO: 16, 27, 28, 29 or 30.

Such yeast may also further comprise:
one or more genes coding for an enzyme having phosphoketolase (PKL) activity (EC 4.1.2.9 or EC 4.1.2.22) or an enzyme having an amino acid sequence according SEQ ID NO: 16, 17, 18, or 19, or functional homologues thereof having a sequence identity of at least 50%, preferably at least 60%, more preferably at least 70%, 75%, 80%, 85%, 90% or 95%, or which functional homologue is derived, by way of one or more amino acid substitutions, deletions or insertions, from the amino acid sequence of SEQ ID NO: 16, 17, 18, or 19;

one or more genes coding for an enzyme having phosphotransacetylase (PTA) activity (EC 2.3.1.8) or an enzyme having an amino acid sequence according SEQ ID NO: 20, 21, 22, or 23, or functional homologues thereof having a sequence identity of at least 50%, preferably at least 60%, more preferably at least 70%, 75%, 80%, 85%, 90% or 95% or which functional homologue is derived, by way of one or more amino acid substitutions, deletions or insertions, from the amino acid sequence of SEQ ID NO: 20, 21, 22, or 23; and/or one or more genes coding for an enzyme having acetate kinase (ACK) activity (EC 2.7.2.12), or an enzyme having an amino acid sequence according SEQ ID NO: 24 or 25, or functional homologues thereof having a sequence identity of at least 50%, preferably at least 60%, more preferably at least 70%, 75%, 80%, 85%, 90% or 95% or which functional homologue is derived, by way of one or more amino acid substitutions, deletions or insertions, from the amino acid sequence of SEQ ID NO: 24 or 25.

As used herein, a phosphoketolase catalyzes at least the conversion of D-xylulose 5-phosphate to D-glyceraldehyde 3-phosphate and acetyl phosphate. The phosphoketolase is involved in at least one of the following reactions:

EC 4.1.2.9: D-xylulose-5-phosphate+phosphate
⇌ acetyl phosphate+D-glyceraldehyde 3-phosphate+H$_2$O (VIII)

D-ribulose-5-phosphate+phosphate ⇌ acetyl phosphate+D-glyceraldehyde 3-phosphate+H$_2$O EC 4.1.2.22: D-fructose 6-phosphate+phosphate
⇌ acetyl phosphate+D-erythrose 4-phosphate+H$_2$O (IX)

A suitable enzymatic assay to measure phosphoketolase activity is described e.g. in Sonderegger et al. (2004, Applied & Environmental Microbiology, 70(5), pp. 2892-2897). In an embodiment the one or more genes coding for an enzyme having phosphoketolase activity encodes an enzyme having an amino acid sequence according to SEQ ID NO: 5, 6, 7 or 8, or a functional homologue thereof having a sequence identity of at least 50%, preferably at least 60%, 70%, 75%, 80%. 85%, 90% or 95%. Suitable nucleic acid sequences coding for an enzyme having phosphoketolase may in be found in an organism selected from the group of *Aspergillus niger, Neurospora crassa, L. casei, L. plantarum, L. plantarum, B. adolescentis, B. bifidum, B. gallicum, B. animalis, B. lactis, L. pentosum, L. acidophilus, P. chrysogenum, A. nidulans, A. clavatus, L. mesenteroides,* and *O. oenii.*

The recombinant cell may comprise one or more (heterologous) genes coding for an enzyme having phosphotransacetylase activity. As used herein, a phosphotransacetylase catalyzes at least the conversion of acetyl phosphate to acetyl-CoA. In an embodiment the one or more genes coding for an enzyme having phosphotransacetylase activity encodes an enzyme having an amino acid sequence according to SEQ ID NO: 9, 10, 11 or 12, or functional homologues thereof having a sequence identity of at least 50% preferably at least 60%, 70%, 75%, 80%. 85%, 90% or 95%. Suitable nucleic acid sequences coding for an enzyme having phosphotransacetylase may in be found in an organism selected from the group of *B. adolescentis, B. subtilis, C. cellulolyticum, C. phytofermentans, B. bifidum, B. animalis, L. mesenteroides, Lactobacillus plantarum, M. thermophila,* and *O. oeniis.*

As used herein, a phosphotransacetylase catalyzes at least the conversion of acetyl phosphate to acetyl-CoA. Suitable nucleic acid sequences coding for an enzyme having phosphotransacetylase may in be found in an organism selected from the group of *B. adolescentis, B. subtilis, C. cellulolyticum, C. phytofermentans, B. bifidum, B. animalis, L. mesenteroides, Lactobacillus plantarum, M. thermophila,* and *O. oeniis.*

As used herein, an acetate kinase catalyzes at least the conversion of acetate to acetyl phosphate.

The above yeast is particularly useful if the composition is a lignocellulosic hydrolysate, and may be constructed using known recombinant expression techniques. The co-factor modification may be effected before, simultaneous or after any of the modifications 1) to 5).

The recombinant yeast cell according to the invention may be subjected to evolutionary engineering to improve its properties. Evolutionary engineering processes are known processes. Evolutionary engineering is a process wherein industrially relevant phenotypes of a microorganism, herein the recombinant yeast cell, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5 (2005) 925-934, WO2008/041840 and WO2009/112472. After the evolutionary engineering the resulting pentose fermenting recombinant yeast cell is isolated. The isolation may be executed in any known manner, e.g. by separation of cells from a recombinant yeast cell broth used in the evolutionary engineering, for instance by taking a cell sample or by filtration or centrifugation.

In an embodiment, the recombinant yeast cell is marker-free. As used herein, the term "marker" refers to a gene encoding a trait or a phenotype which permits the selection of, or the screening for, a host cell containing the marker. Marker-free means that markers are essentially absent in the recombinant yeast cell. Being marker-free is particularly advantageous when antibiotic markers have been used in construction of the recombinant yeast cell and are removed thereafter. Removal of markers may be done using any suitable prior art technique, e.g. intramolecular recombination.

In one embodiment, the industrial recombinant yeast cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant S. cerevisiae strain ATCC 26602 was selected.

The recombinant yeast may comprise those enzymatic activities required for conversion of pyruvate to a desired fermentation product, such as ethanol, butanol (e.g. n-butanol, 2-butanol and isobutanol), lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the recombinant yeast is derived from an industrial recombinant yeast cell. An industrial cell and industrial recombinant yeast cell may be defined as follows. The living environments of (recombinant yeast cell) cells in industrial processes are significantly different from that in the laboratory. Industrial recombinant yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of Saccharomyces cerevisiae. Under adverse industrial conditions, the environmental tolerant strains should allow robust growth and production. Industrial recombinant yeast cell strains are generally more robust towards these changes in environmental conditions which may occur in the applications they are used, such as in the baking industry, brewing industry, wine making and the biofuel ethanol industry. In one embodiment, the industrial recombinant yeast cell is constructed on the basis of an industrial host cell, wherein the construction is conducted as described hereinafter. Examples of industrial yeast cell (S. cerevisiae) are Ethanol Red® (Fermentis) Fermiol® (DSM) and Thermosacc® (Lallemand).

The recombinant yeast is preferably inhibitor tolerant, i.e. they can withstand common inhibitors at the level that they typically have with common pretreatment and hydrolysis conditions, so that the recombinant yeast cells can find broad application, i.e. it has high applicability for different feedstock, different pretreatment methods and different hydrolysis conditions. In an embodiment the recombinant yeast cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

In an embodiment, the recombinant yeast cell is a cell that is naturally capable of alcoholic fermentation, preferably, anaerobic alcoholic fermentation. A recombinant yeast cell preferably has a high tolerance to ethanol, a high tolerance to low pH (i.e. capable of growth at a pH lower than about 5, about 4, about 3, or about 2.5) and towards organic and/or a high tolerance to elevated temperatures.

The recombinant yeast comprises, or is transformed with or is genetically modified with a nucleotide sequence that does not naturally occur in the cell in question. Techniques for the recombinant expression of enzymes in a cell, as well as for the additional genetic modifications of a recombinant yeast cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Abusable et al., eds., "Current protocols in molecular biology", Green Publishing and Wiley Interscience, New York (1987). Methods for transformation and genetic modification of fungal host cells are known from e.g. EP-A-0635574, WO98/46772, WO 99/60102, WO00/37671, WO90/14423, EP-A-0481008, EP-A-0635574 and U.S. Pat. No. 6,265,186.

The process for the production of ethanol is a fermentation process which is preferably run at a temperature that is optimal for the yeast. Thus, for most recombinant yeast cells, the fermentation process is performed at a temperature which is less than about 50° C., less than about 42° C., or less than about 38° C.

The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity.

Recovery of the ethanol is known in the art and may comprise fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol. In an embodiment in addition to the recovery of fermentation product, the yeast may be recycled. The following non-limiting examples are intended to be purely illustrative.

EXAMPLES

Materials and Methods

Media

Fermentations are performed using synthetic (Luttik 2000) and industrial media (corn stover hydrolysate, corn mash). Whenever strains are applied with a histidine auxotrophy, media are supplemented with 200 mg/L histidine. Corn stover hydrolysate medium is prepared by diluting a 17% ds corn stover hydrolysate 1.5-fold with demineralized water and supplementing it with 24 g/L xylose, 1 g/L urea and glycerol at an equimolar quantity to the acetate in the hydrolysate. To prevent outgrowth of any bacterial contaminants present in the hydrolysate, neomycin and penicillin G are added to a final concentration of 50 µg/ml and 100 µg/ml respectively. Approximately 250 µl/l of silicone antifoam (Dow Corning 1520) is added to prevent foaming. The applied hydrolysate was previously dilute-acid pretreated at NREL, pH adjusted (from approximately 1-2) to pH 4.5 using 2M ammonia, and subsequently enzymatically hydrolyzed using DSM's proprietary enzyme cocktail. Prior to fermentation, the pH of the medium is adjusted to 5.5 with 2M KOH.

Corn mash is prepared by mixing 30% w/w ground corn solids (Limagrain Westhove Maize L3) with demineralized water, adjusting the pH to 5.5 with 2M $H_2SO_4$, addition of 0.02% w/w alpha-amylase (Termamyl, Novozymes) and incubating for 4 hours at 80° C. in a rotary shaker (150 RPM). Urea (1.25 g/L) is added as N-source. To mimic acetic acid concentrations found in corn ethanol plants, the mash is supplemented with 1.5 g/L acetic acid, and pH is adjusted to 5.0 using 2M $H_2SO_4$/KOH. At the start of the fermentation, 0.16 g/kg glucoamylase (Spirizyme, Novozymes) is added.

Preculture Conditions

A loopful of frozen (glycerol) stock culture is streaked on YhPD (10 g/l yeast extract, 20 g/l phytone, 20 g/l glucose and 15 g/l agar) plate and incubated for 3 days at 30° C. 3 Colonies are transferred from the agar plate to a 500 ml shake flask containing 200 ml of a mineral medium (Luttik et al., 2000), at pH 6.0, adjusted 6N KOH. Cultures are incubated overnight (17-20 hrs) in a shaker incubator (200 RPM) at 30° C. After the dry cell weight (DCW) content of the culture is determined by filtration (see Dry cell weight determination). A quantity of preculture corresponding to the required inoculation size for the fermentation is centrifuged, (3 min, 13500×g) washed once with one culture volume cold (4° C.) sterile demineralized water, centrifuged once more, resuspended in fermentation medium and transferred to the fermenter.

Fermentation Conditions

Fermentations are performed in DASbox (Eppendorf, Hamburg, Germany) 250 ml mini-bioreactor systems, at 200 ml working volume. Fermentations are temperature-controlled at 32° C., stirred at 300 RPM and, where indicated, pH is limited to the designated upper value by controlled addition of 2M $H_2SO_4$. To ensure anaerobic conditions, the headspace is sparged with 50 ml/min $N_2$.

Strains

Strain YD01437 has been described in detail in PCT/EP2014/068325→WO2015/028583, in particular in examples 6 and 7, strain T5.

Sample Analyses

Dry cell weight is determined by filtering a known quantity of fermentation broth sample over preweighed nitrocellulose filters (pore size 0.45 mm), and washing the yeast biomass with demineralized water, drying for 4 hours at 103° and weighing. Metabolites in the fermentation broth are determined by HPLC analyses on the supernatant of broth samples after centrifugation. The applied method is described in detail in WO2016/097202. For SSF samples, 1 mL/L of a 10 g/L acarbose stock solution is added to the samples to arrest glucoamylase activity.

Example 1

Synthetic Medium

Synthetic medium (luttik 2000), with 10% m/v glucose, 1.5 g/L acetic acid, (starting) pH 5.5, set with 2M KOH. Pitch 0.5 g CDW/L YD01437.
No pH Control (A)

Acetic acid is converted as the strains grows anaerobically, pH rises to approximately 7.0, at which point its conversion stops due to reaching a minimum level of undissociated acetic acid, despite the presence of approximately 0.54 g/L total acetate. Yeast growth therefore either stops or is very slow.
pH Maintained at 5.5 (B)

Acetic acid is converted as the strains grows anaerobically, but pH remains at 5.5. Acetic acid conversion and growth therefore continue for longer (compared to A) until it also reaches the minimum threshold of approximately 50 µM undissociated acetic acid, before glucose is depleted. The total remaining acetate is now much lower; approximately 0.001 g/L, leading to a higher ethanol yield.

Example 2

Lionocellulosic Hydrolysate

Corn stover hydrolysate medium, pitch 0.5 g CDW/L YD01437.
No pH Control (C)

Acetic acid is converted (co-conversion with glycerol), pH rises to 7.1, at which point it is stopped due to reaching a minimum threshold of approximately 50 µM undissociated acetic acid, despite the presence of approximately 2.5 g/L total acetate. Sugar (xylose) conversion continues until depletion.
pH Maintained at 5.5 (D)

Acetic acid is converted (co-conversion with glycerol), but pH remains at 5.5, so acetic acid conversion continues for longer (compared to C) until it also reaches the minimum threshold of approximately 50 µM undissociated acetic acid, before xylose is depleted. The total remaining acetate is now much lower; ~0.02 g/L, leading to a higher ethanol yield.

Example 3

Corn Mash

Corn mash, pitch 0.075 g CDW/L YD01437
No pH Control (C)

Acetic acid is converted as the strains grows anaerobically, pH rises to 7.0, at which point it is stopped due to reaching a minimum threshold of approximately 50 µM undissociated acetic acid, despite the presence of residual total acetate. Yeast growth either stops or is very slow due to the absence of redox sink. Free glucose will build up due to the lack of growth, presenting osmostress to the yeast. Glucose conversion progresses at incrementally slower rate or might stop altogether.
pH Maintained at 5.5 (D)

Acetic acid is converted as the strains grows anaerobically, but pH remains at 5.5, so acetic acid conversion continues for longer (compared to C) until it also reaches the minimum threshold of approximately 50 µM undissociated acetic acid, before glucose is depleted. The total remaining acetate is now much lower; approximately 0.001 g/L, leading to a higher ethanol yield.

The invention claimed is:

1. A process for production of ethanol from a composition comprising glucose and between 50 μM and 100 mM acetic acid, said process comprising:
    fermenting said composition until the amount of undissociated acetic acid is 1 mM or less in the presence of a recombinant yeast which comprises an exogenous glycerol transporter and is capable of converting acetic acid anaerobically;
    monitoring the amount of undissociated acetic acid in the composition during the fermentation;
    adding acid to the composition to maintain the amount of undissociated acetic acid at a value ≥50 μM and ≤1 mM for the remainder of the fermentation; and
    recovering the ethanol.

2. The process according to claim 1 wherein the recombinant yeast comprises:
    a nucleic acid sequence encoding an enzyme having acetylating acetaldehyde dehydrogenase activity (EC 1.2.1.10 or EC 1.1.1.2);
    a nucleic acid sequence encoding an an enzyme having acetyl-CoA synthetase activity (E.C.6.2. 1.1); and optionally
    a nucleic acid sequence encoding an enzyme having NAD-dependent alcohol dehydrogenase activity (EC 1.1.1.1).

3. The process according to claim 1 wherein the recombinant yeast comprises a nucleic acid sequence encoding an enzyme having glycerol dehydrogenase activity.

4. The process according to claim 1 wherein the recombinant yeast comprises a nucleic acid coding for an enzyme having dihydroxyacetone kinase activity.

5. The process according to claim 1 wherein the recombinant yeast comprises a deletion or disruption of one or more endogenous nucleotide sequences encoding a glycerol-3-phosphate dehydrogenase.

6. The process according to claim 1 wherein the recombinant yeast comprises a deletion or disruption of one or more endogenous nucleotide sequences encoding a glycerol 3-phosphate phosphohydrolase, optionally *S. cerevisiae* GPP1 or GPP2.

7. The process according to claim 1 wherein the recombinant yeast comprises a deletion or disruption of one or more endogenous nucleotide sequences encoding an aldehyde dehydrogenase or which yeast has reduced aldehyde dehydrogenase activity compared to its corresponding wild-type yeast.

8. The process according to claim 7 wherein said nucleotide sequences encode aldehyde dehydrogenase ALD2, ALD3, ALD4, ALD5, and/or ALD6.

9. The process according to claim 7 wherein the yeast further comprises:
    one or more genes coding for an enzyme having phosphoketolase (PKL) activity (EC 4.1.2.9 or EC 4.1.2.22) or an enzyme having an amino acid sequence according SEQ ID NO: 5, 6, 7, or 8, or functional homologues thereof having a sequence identity of at least 70%,
    one or more genes coding for an enzyme having phosphotransacetylase (PTA) activity (EC 2.3.1.8) or an enzyme having an amino acid sequence according SEQ ID NO: 9, 10, 11, or 12, or functional homologues thereof having a sequence identity of at least 70%; and/or
    one or more genes coding for an enzyme having acetate kinase (ACK) activity (EC 2.7.2.12), or an enzyme having an amino acid sequence according SEQ ID NO: 1 or 2, or functional homologues thereof having a sequence identity of at least 70%.

10. The process according to claim 1, wherein the composition is a lignocellulosic biomass hydrolysate.

11. The process according to claim 1, wherein the composition is a starch hydrolysate, optionally a corn starch hydrolysate.

12. The process according to claim 1, wherein the yeast is a *Saccharomyces cerevisiae*.

\* \* \* \* \*